United States Patent [19]

Moss et al.

[11] Patent Number: 5,386,021

[45] Date of Patent: Jan. 31, 1995

[54] MAMMALIAN GUANINE NUCLEOTIDE BINDING PROTEIN WITH AN ADP-RYBOSYLATION FACTOR DOMAIN

[75] Inventors: Joel Moss, Bethesda; Koichi Mishima, Rockville; Maria S. Nightingale, Bethesda, all of Md.; Mikako Tsuchiya, Izumo, Japan

[73] Assignee: The United States of America, as represented by the Department of Health & Human Services, Washington, D.C.

[21] Appl. No.: 49,473

[22] Filed: Apr. 19, 1993

Related U.S. Application Data

[63] Continuation-in-part of Ser. No. 49,252, Apr. 16, 1993, abandoned.

[51] Int. Cl.$^6$ .............................................. C07H 17/00
[52] U.S. Cl. ................................. 536/23.1; 536/23.5; 435/6; 435/69.1; 435/172.3
[58] Field of Search .................. 536/23.1, 23.5; 435/6, 435/69.1, 71.1, 172.3, 270, 320.1

[56] References Cited

PUBLICATIONS

Bobak, et al. "Molecular cloning, characterization, and expression of human ADP-ribosylation factors: Two guanine nucleotide-dependent activators of cholera toxin" *Proc. Natl. Acad. Sci.* USA 86: pp. 6101–6105 (1989).

Boman, et al. "A role for ADP-ribosylation factor in nuclear vesicle dynamics" *Nature* 358: pp. 512–514 (1992).

Kahn, et al. "The Amino Terminus of ADP-ribosylation Factor (ARF) Is a Critical Determinant of ARF Activities and Is a Potent and Specific Inhibitor of Protein Transport" *J. Biol. Chem.* 267:18 pp. 13039–13046 (1992).

Kahn, et al. "Human ADP-Ribosylation Factors" *J. Biol. Chem.* 266:4 pp 2606–2614 (1991).

Lee, et al. "Characterization of the Human Gene Encoding ADP-ribosylation Factor 1, a Guanine Nucleotide-binding Activator of Cholera Toxin" *J. Biol. Chem.* 267:13 pp. 9028–9034 (1990).

Monaco, et al. Abstract: "Identification of a New form of ADP-ribosylation Factor by Poly Chain Reaction *Proc. Natl. Acad. Sci* USA 87: pp. 2206–2210 (1990).

Monaco, et al. "Selective amplification of an mRNA and related pseudogene for a human ADP-ribosylation factor, a guanine nucleotide-dependent protein activator of cholera toxin" *Proc. Natl. Acad. Sci.* USA 87: pp. 2206–2210 (1990).

Murtagh, et al. "Guanine Nucleotide-binding Proteins in the Intestinal Parasite *Giardia lamblia*" *J. Biolog. Chem.* 267:14 pp. 9654–9662 (1992).

Price, et al. "Effects of Phospholipid and GTP on Recombinant ADP-ribosylation Factors (ARFS)" *J. Biolog. Chem.* 267:25 pp. 17766–17772 (1992).

Price, et al. "Guanine nucleotide-binding proteins that enhance choleragen ADP-ribosyltransferase activity: Nucleotide and deduced amino acid sequence of an DP-ribosylation factor cDNA" *Proc. Natl. Acad. Sci.* USA 85: pp. 5488–5491 (1988).

Serafini, et al. "ADP-ribosylation Factor is a Subunit of the Coat of Golgi-derived COP-coated Vesicles: A Novel Role for a GTP-binding Protein" *Cell* 67: pp. 239–253 (1991).

Sewell, et al. "Sequences of the Bovine and yeast ADP-ribosylation factor and comparison to other GTP--binding proteins" *proc. natl. Acad. Sci.* USA 85: pp. 4620–4624 (1988).

Stearns, et al. "ADP-ribosylation factor is functionally and physically associated with the Golgi complex" *Proc. Natl. Acad. Sci.* USA 87: pp. 1238–1242 (1990).

Tsai, et al. "Isolation and Characterization of the Human Gene for ADP-ribosylation Factor 3, a 20-kDa Guanine Nucleotide-binding Protein Activator of Cholera Toxin" *J. Biol. Chem.* 266:34 pp. 23053–23059 (1991).

Tsai, et al. "Stimulation of Choleragen Enzymatic Activities by GTP and Two Soluble Proteins Purified from Bovine Brain" *J.Biol. Chem.* 263:4 1768–1772 (1988).

Tsuchiya, et al. "Molecular Identification of ADP-Ribosylation Factor mRNAs and Their Expression in Mammalian Cells" *J. Biolog. Chem.* 266:5 pp. 2772–2777 (1991).

Tsuchiya, et al. "Tissue and Species Distribution of mRNA Encoding Two ADP-ribosylation Factors, 20-kDa Guanine Nucleotide Binding Proteins" *Biochemistry* 28: pp. 9668–9673 (1989).

*Primary Examiner*—Christine M. Nucker
*Assistant Examiner*—Laurie Scheiner
*Attorney, Agent, or Firm*—Knobbe, Martens, Olson & Bear

[57] ABSTRACT

The invention provides a method for detecting the presence of ARD 1 protein in a sample. The method includes the steps of providing labeled or immobilized anti-ARD 1 antibody in a reaction zone, introducing sample into the reaction zone such that ARD 1 protein in the sample, if present, will react with said antibody to form an immunological complex, and detecting the formation of said immunological complex. Cells, nucleotide and amino acid sequences and vectors associated with ARD 1 are also described.

5 Claims, 7 Drawing Sheets

```
                                            10         20         30         40         50         60         70
SEQ.ID NO:27 hARF1    1  MGNIFANLFK GLFGKKEMRI LMVGLDAAGK TTILYKLKLG EIVTTIPTIG FNVETVEYKN ISFTVWDVGG
SEQ.ID NO:28 bARF2    1  ***V*EK*** S********* ********** ********** ********** ********** **********
SEQ.ID NO:29 hARF3    1  *GL*** S*I***** ****** ****** ****** ****** ********
SEQ.ID NO:30 hARF4    1  LTISSS R****Q ******** ****** ****** ******** *C********
SEQ.ID NO:31 hARF5    1  LTVSAS RI***Q ******** ****** ****** ******** *C********
SEQ.ID NO:32 hARF6    1  KVLSK--- --IFN* L***** ****** QS****V* ****T* VK*N******
SEQ.ID NO:33 hARD1  403  *--------- -------I*V VTL*G* ***F*QD *FMQP*** ****** LKI*****

80         90        100        110        120        130        140
hARF1    71  QDKIRPLWRH YFQNTQGLIF VVDSNDRERV NEAREELMRM LAEDELRDAV LLVFANKQDL PNAMNAAEIT
bARF2    71  ******** ****** ****** T***** ****** *V ********
hARF3    71  ********** ********** ********** ********** ********** ********** **********
hARF4    71  R*** ****** ******I Q*VAD**QK* L*** L* **AIS*M*
hARF5    71  ********** ********** ********** Q*SAD**QK* *Q******** ********M ****PVS*L*
hARF6    67  *YTG****** *YL***AVV* *CAD*I D*QH*I INDR*M****I I*I******* *DKPHQ
hARD1   457  KH*L****K* *YL***AVV* *****SH*D*I SHSAKL *T*K***L I******V AG*LSVE***

150        160        170        180
hARF1   141  DKIGLHSL-R HRNWYIQATC ATSGDGLYEG LDWL-SNQLR NQK        181
bARF2   141  ********-* Q********* ********** *****-****K ***        181
hARF3   141  ********-* ********** ********** *****-A***K *K*        181
hARF4   141  *****Q**-* N*T***V*** **Q*T***** ****-*E*S  KR         180
hARF5   141  *****QH*-* S*T***V*** **Q*T***D* ****-HE*S  KR         180
hARF6   135  E****TRI-* D****V*PS* ********** *T***T**YKS           175
hARD1   528  EL*S**K*CC G*S****GCD *RM*** *RQ*V AAGDLDVA        574

FIG.1
```

MAMMALIAN GUANINE NUCLEOTIDE BINDING PROTEIN WITH AN ADP-RYBOSYLATION FACTOR DOMAIN

This is a continuation-in-part of the parent application, U.S. application Ser. No. 08/049,252, filed Apr. 16, 1993.

BACKGROUND

Monomeric guanine nucleotide-binding proteins of the ras superfamily of 18-30 kDa function in a variety of cellular processes including signaling, growth, immunity, and protein transport (Barbacid, H. Annu. Rev. Biochem. 56: 779-828 (1987); Bourne, H. R. Cell 53:669-671 (1988); Bourne, et al. Nature (London) 349: 117-127 (1991); Gabig, et al. J. Biol. Chem. 262: 1685-1690 (1987); Goud, et al. Nature (London) 345: 553-556 (1990); Hall, A. Science 249: 635-640 (1990); Knaus, et al. Science 254: 1512-1515 (1991)). ADP-ribosylation factors (ARFs) constitute one family of the ras superfamily.

ARF was initially identified as a factor required for cholera toxdin-catalyzed ADP-ribosylation of $G_{s\alpha}$, the stimulatory guanine nucleotide-binding (G) protein of the adenylylcyclase system (Kahn, et al. J. Biol. Chem. 259: 6228-6234 (1984); Serventi, et al. In: Current Topics in Microbiology and Immunology 175, (Aktories, K. ed) pp. 43-67, Springer-Verlag, Berlin Heidelberg (1992). In the presence of GTP or a nonhydrolyzable GTP analogue, ARF serves as an allosteric activator of cholera toxin ADP-ribosyltransferase (Noda, et al. Biochim. Biophys. Acta 1034: 195-199 (1990); Tsai, et al. J. Biol. Chem. 263: 1768-1772 (1988); Tsai, et al. Proc. Natl. Acad. Sci. (USA) 84: 5139-5142 (1987)). It stimulates the toxin-catalyzed ADP-ribosylation of proteins unrelated to $G_{s\alpha}$ and simple guanidino compounds such as arginine and agmatine as well as auto-ADP-ribosylation of the toxin A1 protein (Noda, et al. Biochim. Biophys. Acta 1034: 195-199 (1990); Tsai, et al. J. Biol. Chem. 263: 1768-1772 (1988); Tsai, et al. Proc. Natl. Acad. Sci. (USA) 84: 5139-5142 (1987)).

ARFs are evolutionarily well conserved and present in all eukaryotes from Giardia to mammals (Kahn, et al. J. Biol. Chem. 263: 8282-8287 (1988); Murtagh, et al. J. Biol. Chem. 267: 9654-9662 (1992); Tsai, et al. J. Biol. Chem. 266: 8213-8219 (1991); Tsuchiya, et al. Biochemistry 28: 9668-9673 (1989); Tsuchiya, et al. J. Biol. Chem. 266: 2772-2777 (1991)). Immunologically, they have been localized to the Golgi apparatus of several types of cells (Stearns et al. Proc. Natl. Acad. Sci. (USA) 87: 1238-1242 (1990)). ARFs are required for association of nonclathrin coat proteins with intracellular transport vesicles (Serafini, et al. Cell 67: 239-253 (1991)) and also appear to be critical during an early step in endocytosis as well as in nuclear vesicle fusion (Boman, et al. Nature (London) 358: 512-514 (1992); Lenhard, et al. J. Biol. Chem. 267: 13047-13052 (1992)). GTP binding and hydrolysis may be involved in binding of ARF to membranes, and the nonhydrolyzable GTP analogue GTP$\gamma$S, but not GTP or GDP, promotes the association of cytosolic ARF with Golgi (Regazzi, et al. Biochem. J. 275: 639-644 (1991)) or phospholipid membranes (Kahn, et al. J. Biol. Chem. 266: 15595-15597 (1991); Walker, et al. J. Biol. Chem. 267: 3230-3235 (1992)).

By molecular cloning from cDNA and genomic libraries, and PCR amplification of RNA transcripts, six mammalian ARFs, two yeast ARFs, and two Giardia ARFs have been identified (Bobak, et al. Proc. Natl. Acad. Sci. (USA) 86: 6101-6105 (1989); Monaco, et al. Proc. Natl. Acad. Sci. (USA) 87: 2206-2210 (1990); Murtagh, et al. J. Biol. Chem. 267: 9654-9662 (1992); Price, et al. Proc. Natl. Acad. Sci. (USA) 85: 5488-5491 (1988); Sewell, et al. Proc. Natl. Acad. Sci. (USA) 85: 4620-4624 (1988); Stearns, et al. Mol. Cell. Biol. 10: 6690-6699 (1990); Tsuchiya, et al. J. Biol. Chem. 266: 2772-2777 (1991)). Mammalian ARFs fall into three classes based on deduced amino acid sequences, gene structure, phylogenetic analysis, and size (Lee, et al. J. Biol. Chem. 267: 9028-9034 (1992); Tsuchiya, et al. J. Biol. Chem. 266: 2772-2777 (1991)). Class I ARFs are ARFs 1-3; class II includes ARFs 4 and 5; and class III has ARFs 6. Some lipids and/or detergents, e.g., SDS, cardiolipin, dimyristoylphosphatidylcholine (DMPC)/cholate, enhance ARF activities (Bobak, et al. Biochemistry 29: 855-861 (1990); Noda, et al. Biochim. Biophys. Acta 1034: 195-199 (1990); Tsai, et al. J. Biol. Chem. 263: 1768-1772 (1988)). Members of the ARF multigene family, when expressed as recombinant proteins in E. coli, display different phospholipid and detergent requirements (Price, et al. J. Biol. Chem. 267: 17766-17772 (1992)). Following synthesis in E. coli all of these ARFs had enhanced cholera toxin ADP-ribosyltransferase activity in the presence of GTP (Kahn, et al. J. Biol. Chem. 266: 2606-2614 (1991); Price, et al. J. Biol. Chem. 267: 17766-17772 (1992); Weiss, et al. J. Biol. Chem. 264: 21066-21072 (1989)).

In general, differences in the various ARF sequences are concentrated in the amino-terminal regions and the carboxyl portions of the proteins. Only three of 17 amino acids includin Met$^1$ and Gly$^2$, in the amino termini are identical among ARFs, and four amino acids in this region of ARFs 1-5 are missing in ARF 6 (Tsuchiya, et al. J. Biol. Chem. 266: 2772-2777 (1991)). It was recently reported (Kahn, et al. J. Biol. Chem. 267: 13039-13046 (1992)) that the amino-terminal regions of ARF proteins form an $\alpha$-helix, and that this domain is required for membrane targeting, interaction with lipid, and ARF activity.

Schliefer et al., (J. Biol. Chem. 257: 20-23 (1991)) described a protein distinctly larger than ARF that possessed ARF-like activity. At the time of those studies however, it had not been demonstrated that ARF requires GTP for activity, so functional characterization of the protein did not include assessment of that property.

SUMMARY

The present invention relates to a novel 64 kDa protein styled ARD 1. This protein includes an 18 kDa region that exhibits significant homology to known ADP-ribosylation factors (ARFs), but lacks a 15 amino acid domain previously thought necessary for ARF stimulation. The remaining 46 kDa sequence is apparently unlike any known protein. Both rat and human sequences are specifically disclosed.

One aspect of the present invention, therefore, comprises a polynucleotide encoding ARD 1 (which substantially has the sequence of SEQ ID NO:1 or which otherwise substantially encodes the sequence of SEQ ID NO:2) in isolated or purified form. An isolated polynucleotide is one that has been largely separated from other nucleotides, so that the polynucleotide in any composition of which it is a part is at least 1%, preferably 5% or 10%, and more preferably at least about 20%, 30%, or 50% the particular polynucleotide of interest. Mammalian ARD 1 sequences are of particular interest, and vertebrate sequences such as rat and human sequences are particularly preferred.

The present invention also includes a recombinant DNA sequence in the form of a nucleic acid expression vector, comprising the DNA of SEQ ID NO:1 operably linked to a promoter. The promoter may be a heterologous promoter, for example, and is preferably adapted to direct expression of the polynucleotide in a host cell.

The present invention also includes a cell transfected with the expression vector discussed above. Such a cell is preferably capable of expressing ARD 1 protein. Secretion sequences of the type well known in the art may be included in the expression vector that are adapted to promote secretion of the protein in the cell in question. Although the transfected cell may be procaryotic, it is preferably a eukaryotic cell line. CHO cells, for example, are suitable for use in the present invention. Other mammalian cell lines, including human cell lines, may be used, as well other vertebrate cell lines. Alternatively, insect cell lines may be used for expressing the protein of the present invention.

One preferred embodiment of the present invention is an ARD 1 protein composition, comprising the polypeptide of SEQ ID NO:2 in a concentration of at least about 0.01 µg/g. The composition of claim 3, wherein the polypeptide is in substantially purified form.

Also disclosed is an immunoassay kit, comprising ARD 1 protein as a polypeptide reagent, a reaction unit including a reaction zone in which the polypeptide reagent can interact with antibodies (if any) in the sample directed against ARD 1 to form an immunological complex, and means for detecting the reaction or lack of reaction of the polypeptide with the antibodies. Similarly, the present invention includes an immunoassay kit where anti-ARD 1 antibodies are used as a reagent to react with ARD 1 (if any) in a sample, and the reaction of the antibody and ARD 1 are detected.

Another aspect of the present invention relates to isolated or purified antibody against ARD 1 protein. Both polyclonal antibody and monoclonal antibody against ARD 1 protein are contemplated. Moreover, the monoclonal antibody of the present invention is not necessarily isolated or purified.

A further aspect of the present invention is a method for detecting the presence of ARD 1 protein in a sample, comprising the steps of providing labeled or immobilized anti-ARD 1 antibody in a reaction zone, introducing sample into the reaction zone such that ARD 1 protein in the sample, if present, will react with the antibody to form an immunological complex, and detecting the formation of the immunological complex.

BRIEF DESCRIPTION OF THE FIGURES

FIG. 1 is a table showing a comparison of amino acid sequences of ARD 1 and mammalian ARFs. The deduced amino acid sequence of reported human and bovine ARFs and the ARF domain of human ARD 1 were aligned using PC/Gene CLUSTAL. hARF 1, human ARF (Bobak, et al. *Proc. Natl. Acad. Sci.* (USA) 86: 6101–6105 (1989)); bARF 2, bovine ARF 2 (Price, et al. *Proc. Natl. Acad. Sci.* (USA) 85: 5488–5491 (1988); hARF 3, human ARF 3 ((Bobak, et al. *Proc. Natl. Acad. Sci.* (USA) 86: 6101–6105 (1989)); hARF 4 human ARF 4 (Monaco, et al. *Proc. Natl. Acad. Sci.* (USA) 87: 2206–2210 (1990)); hARF 5 and hARF 6, human ARF 5 and human ARF 6, respectively (Tsuchiya, et al. *J. Biol. Chem.* 266: 2772–2777 (1991)); hARD 1, the ARF domain of human ARD 1. Gap penalty and window size were both 10. Asterisks and hyphens indicate amino acids identical to hARF 1 and gaps, respectively.

DETAILED DESCRIPTION

Figure 2:
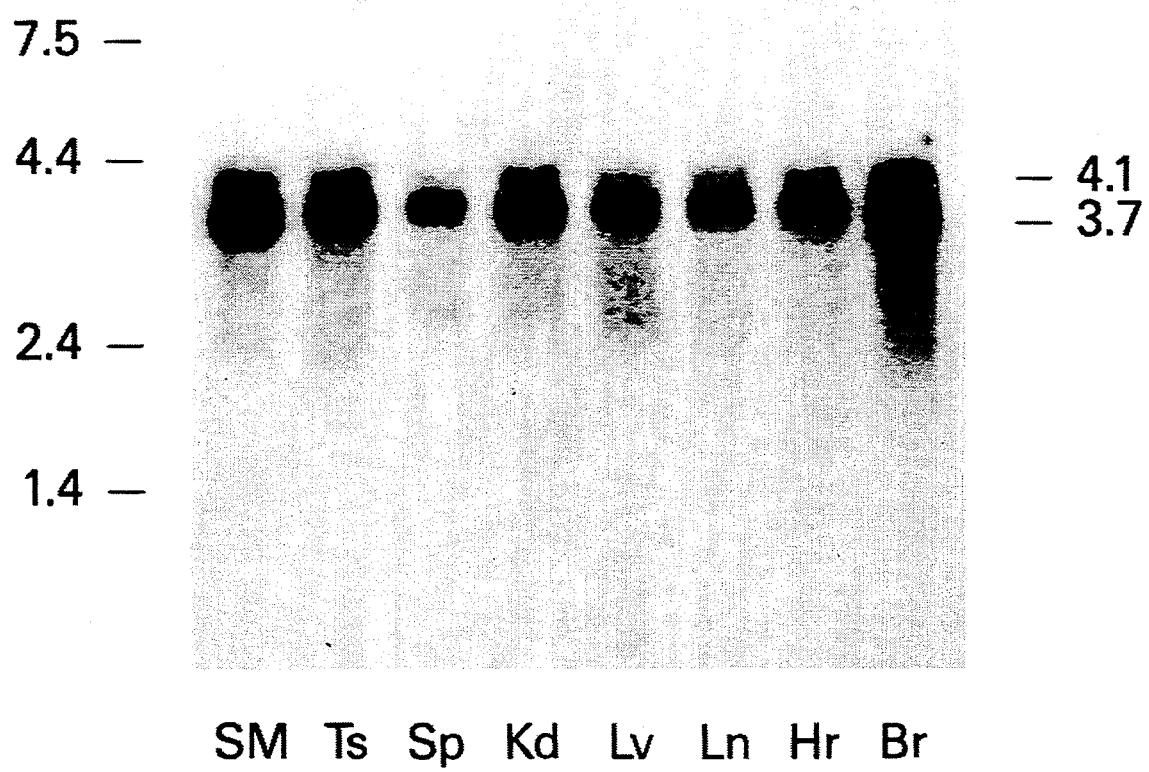
FIG. 2 is a copy of a Northern blot showing the hybridization of poly(A)+ RNA from rat tissues with ARD 1 coding region cDNA. Poly(A)+ RNA from rat skeletal muscle (SM), testis (Ts), spleen (Sp), kidney (Kd), liver (Lv), lung (Ln), heart (Hr) and brain (Br) was hybridized with human ARD 1 coding region cDNA. Positions (kb) of standards (left and ARD 1 mRNA (3.7, 4.1, right) are indicated.

The present invention includes the discovery of a newly recognized member of the ADP-ribosylation factor (ARF) super family termed ARD 1. We have isolated the polynucleotide encoding ARD 1 from both human and rat libraries, as described below. In addition, ARD 1 has been transfected into a host cell and expressed. Upon expression, a 64-kDa guanine nucleotide-binding protein containing an 18-kDa, functional ARF domain at its carboxy terminus termed ARD 1 (for ARF domain) was found.

Recombinant human ARD 1, and a recombinant truncated species containing only the ARF domain following expression, activated cholera toxin ADP-ribosyltransferase in a GTP-dependent manner, consistent with the conclusion that 15 amino acids adjacent to the amino terminus of ARF proteins are not required for toxin activation.

The ARD 1 protein of the present invention is useful for stimulation of cholera toxin ADP-ribosyltransferase. Thus, as a reagent for synthetic biochemistry, it can stimulate toxin-catalyzed ribosylation of such molecules as agmatine in a GTP-dependent manner. It can also be used as a reagent in diagnosis of ADP-ribosylation deficiency disease. ARD 1 includes a GTP binding region, and may be used for binding GTP. It is also useful for generation of anti-ARD 1 antibodies, and as a reagent in assays for ARD 1 and for antibodies against ARD 1. Moreover, ARD 1 is a member of the ARF superfamily, and may be used in general in the same way as known ARF proteins.

ARD 1, a new member of the ARF family, was identified by molecular cloning from cDNA libraries and by Rapid Amplification of cDNA Ends (RACE) type PCR. Nucleotide and amino acid sequences of human and rat ARD 1 are, respectively, 92% and 96% identical. In all rat tissues tested, 3.7-kb and 4.1-kb ARD 1 mRNAs were detected. A cDNA probe specific for the ARD 1 coding region hybridized with poly(A)+ RNA of similar sizes from rat, mouse and rabbit brains, and human cultured cells. The specific probe additionally hybridized to a somewhat different size mRNA from chicken brain. Sequence and hybridization data are thus consistent with the conclusion that these ARF-related proteins are highly conserved in eukaryotic cells.

The unique 64-kDa ARD 1 protein is much larger than other monomeric guanine nucleotide-binding proteins and consists of two distinct domains. One domain is a carboxy-terminal ARF domain and the remainder, doesn't have homology with other known ARF domains. In fact, the sequence of the non-ARF domain has no homology to any sequences in the GenBank data base and contains no motif known to be conserved in any guanine nucleotide-binding proteins.

These conserved motifs, denoted $GX_1X_2X_3X_4GK$, $DX_1X_2G$, and NKXD using the single letter amino acid code, are conserved in other GTP-binding proteins including heterotrimeric G proteins, and ras, rho, and rab proteins. Unlike rab, ras, rho, and $G_{60}$, ARF and ARD 1 have an Aspartic Acid (D) at position $X_2$ in $GX_1X_2X_3X_4GK$. Like $G_{60}$, but unlike the ras super family, $X_1$ and $X_2$ in the $DX_1X_2G$ sequence of ARD 1 and ARFs are Valine (V) and Glycine (G), respectively. The ARF domain contains several motifs common to all ARFs, such as GLDGAGK, DVGG, and NKQD, which are considered to be responsible for GTP-binding (see FIG. 1). The CAT sequence is, however, represented by DAR. The conserved alanine, based on homology to ras, is thought to be involved in guanine nucleotide-binding. In fact, a recombinant protein, representing the ARF domain of ARD 1 had the ability to bind GTP, while the entire ARD 1 protein, under the same conditions did not bind GTP. The reason is unclear, although it is possible that when bound to a nitrocellulose membrane, the conformation of the larger protein limits accessibility of GTP to the binding site.

It has been suggested that the amino terminus of ARF is critical for its function, since mutant ARF 1 protein lacking the amino-terminal 17 amino acids was unable to stimulate cholera toxin-catalyzed ADP-ribosylation of $G_{S\alpha}$ in the presence of DMPC/cholate, although it still possessed GTPγS binding activity that no longer required DMPC/cholate (Kahn, et al. *J. Biol. Chem.* 267: 13039–13046 (1992)). Similarly, ARD 1 fusion protein or its ARF domain fusion protein did not have demonstrable ARF activity in the presence of SDS, DMPC/cholate or cardiolipin, all of which are effective in supporting activity of ARFs (Noda, et al. *Biochim. Biophys. Acta* 1034: 195–199 (1990); Serventi, et al. *In: Current Topics in Microbiology and Immunology* 175, (Aktories, K. ed) pp. 43–67, Springer-Verlag, Berlin Heidelberg (1992); Tsai, et al. *Proc. Natl. Acad. Sci.* (USA) 84: 5139–5142 (1987)).

In the presence of Tween 20, however, ARD 1 protein stimulated toxin-catalyzed ADP-ribosylation of agmatine in a GTP-dependent manner. Removal of the non-ARF domain from ARD 1 protein significantly diminished its ARF activity and increased the GTP concentration required for half maximal activity, suggesting some role for the non-ARF domain in its ARF-like activity. Clearly, however, these data are consistent with the notion that toxin activation does not require the amino-terminal 15 amino acids of ARF, although they may contribute to interaction with phospholipids.

As a first step, we isolated cDNA from a human HL-60 lambda library that had homology with known ARF sequences.

Materials $[\alpha^{-32}P]dATP$ (6,000 Ci/mmol), $[\alpha\text{-thio}^{35}S]dATP$ (1,350 Ci/mmol), and $[\alpha^{-32}P]GTP$ (800 Ci/mmol) were purchased from DuPont-New England Nuclear; [adenine-$^{14}C$]NAD (273 Ci/mol) from Amersham (Arlington Heights, Ill.); random-primed DNA labeling kit and GDPβS from Boehringer Mannheim (Indianapolis, IN); human fetal brain cDNA and rat brain cDNA Lambda ZAP library from Stratagene (La Jolla, Calif.); competent *E. coli* DH5α (maximal efficiency), terminal deoxynucleotidyl transferase and pSPORT 1 from Life Technology (Gaithersburg, Md.); plasmid purification kit from Qiagen (Chatsworth, Calif.); DNA sequencing kit from United States Biochemical Corp. (Cleveland, Ohio); AMV reverse transcriptase, NotI, SalI, RNase inhibitor (RNasin) and T4 DNA ligase from Promega (Madison, Wis.); Centricon 100 from Amicon (Danvers, Mass.); nylon membrane (Nytran) and nitrocellulose membrane from Schleicher and Schuell (Keene, NH); Thermus aquaticus DNA polymerase from Perkin-Elmer/Cetus (Norwalk, Conn.); glutathione, glutathione-agarose, cardiolipin, DMPC, cholate, and NAD from Sigma (St. Louis, Mo.); and AG1-X2 from Bio-Rad (Richmond, Calif.). Oligonucleotides were synthesized using an Applied Biosystems 380B DNA synthesizer.

Experiment 1

Analysis of ARD 1 cDNA

A cyclic, AMP-differentiated HL-60 Lambda ZAP library (5 ×10$^5$ plaques) was screened by plaque hybridization with ARF 2B cDNA (Price, et al. *Proc. Natl. Acad. Sci.* (USA) 85: 5488–5491 (1988)) and a mixture of oligonucleotides denoted XARFC as described by Tsuchiya et al., (*J. Biol. Chem.* 266: 2772–2777 (1991)). The only clone (#76) that was positive with the ARF 2B cDNA and negative with oligonucleotides specific for ARFs 1-6 (Tsuchiya et al., *J. Biol. Chem.* 266: 2772–2777 (1991)) was plaque-purified, the insert was excised in vivo by the method of Short et al.(*Nucleic Acids Res.* 16: 7583–7600 (1988)). The insert was then purified using Qiagen, and sequenced by the Sanger et al. method (*Proc. Natl. Acad. Sci.* (USA) 74: 5463–5467 (1977)). The 1660-bp insert (nucleotides 706–2365 in Table I) included an open reading frame (1207–1722) encoding an ARF domain of 172 amino acids.

TABLE I

Nucleotide and Protein Alignment of Human and Rat ARD I

| | | | | | | | -22 CTGTGTGGCGCTTCCCTGCGAGG | |
|---|---|---|---|---|---|---|---|---|
| HUMAN (SEQ ID NO:2) | | | | | | | G R Q G S | R G T A V V K V L E |
| HUMAN (SEQ ID NO:1) | 1 | M A T L V V N K L G | A G V D S | GCGGGAGTAGACAGTGGCCGGCAGGCAGC | CGGGGACAGCTGTAGTGAAGGTGCTAGAG |
| | 1 | ATGGCTACCCTGGTTGTAAACAAGCTCGGA | | | |
| RAT | | | | | | | | |
| HUMAN | 31 | C G V C E D V F S L | Q G D K V P R L L L | C G H T V C H D C L |
| HUMAN | 91 | TGTGGAGTTTGTGAAGATGTCTTTTCTTTG | CAAGGAGACAAAGTTCCCCGTCTTTTGCTT | TGTGGCCATACCGTCTGTCATGACTGTCTC |
| RAT | | ---T--- | ---T--C-- | ---G--- |
| HUMAN | 61 | T R L P L H G R A I | R C P F D R Q V T D | L G D S G V W G L K |
| HUMAN | 181 | ACTCGCCTACCTCTTCATGGAAGAGCAATC | CGTTGCCCATTTGATCGACAAGTAACAGAC | CTAGGTGATTCAGGTGTCTGGGGATTGAAA |
| RAT | | ---T--G--A-- | ---G--- | ---C-A--- ---T--- |
| HUMAN | 91 | K N F A L E L L L E | R L Q N G P I G Q Y | G A A E B S I G I S |
| HUMAN | 271 | AAAAATTTGCTTTATTGGAGCTTTTGGAA | CGACTGCAGAATGGGCCTATTGGTCAGTAT | GGAGCTGCAGAAGAATCCATTGGGATATCT |
| RAT | | ---C---A-- | ---TT---A---A--A-- | ---G--C--- |
| HUMAN | 121 | G E S I R C D E D | E A H L A S V Y C T | V C A T H L C S E C |
| HUMAN | 361 | GGAGAGAGCATCATTCGTTGTGATGAAGAT | GAAGCTCACCTTGCCTCTGTATATTGCACT | GTGTGTGCAACTTGTGCTCTGAGTGT |
| RAT | | ---T--- | ---G--- ---A--- | ---G--- ---A--- |
| HUMAN | 151 | S Q V T H S T X T L | A K H R R V P L A D | K P H E K T M C S Q |
| HUMAN | 451 | TCTCAAGTTACTCATTCTACAAAGACATTA | GCAAAGCACAGGCGAGTTCCTCTAGCTGAT | AAACCTCATGAGAAAACTATGTGTCTCAG |
| RAT | | ---TC-G | ---C--- ---G--C-- | ---C--- G |
| HUMAN | 181 | H Q V H A I E F V C | L E B G C Q T S P L | M C C V C K E Y G K |
| HUMAN | 541 | CACCAGGTGCATGCCATTGAGTTTGTTTGC | TTGGAAGAAGGTTGTCAAACTAGCCCACTC | ATGTGCTGTGTCTGCAAAGAATATGGAAAA |
| RAT | | ---A--- | ---T-T-- | |
| HUMAN | 211 | H Q G H K H S V L E | P E A N Q I R A S I | L D M A R C I R T F |
| HUMAN | 631 | CACCAGGGTCACAAGCATTCAGTATTGGAA | CCAGAAGCTAATCAGATCCGAGCATCAATT | TTAGATATGGCTACTGCATACGGACCTTC |
| RAT | | ---C--- ---C-- G | ---G--- | ---A--- |
| HUMAN | 241 | T E E I S D Y S R K | L V G I V Q H I B G | G E Q I V E D G I G |
| HUMAN | 721 | ACAGAGGAAATCTCAGATTATTCCAGAAAA | TTAGTTGGAATTGTGCAGCACATTGAAGGA | GGAGAACAAATCGTGGAAGATGGAATTGGA |
| RAT | | ---G--- | ---T--- | ---A--- |
| HUMAN | 271 | M A H T E H V P G T | A E N A R S C I R A | Y F Y D L H E T L C |
| HUMAN | 811 | ATGGCTCACACAGAACATGTACCAGGGACT | GCAGAGAATGCCCGGTCATGTATTCGAGCT | TATTTTTATGATCTACATGAAACTCTGTCT |
| RAT | | ---G--- ---C--C--T-- | ---A--- ---A--- ---G-CA-- | ---C--- ---T-G-- |
| HUMAN | 301 | R Q E M A L S V V | D A H V R E K L I W | L R Q Q Q E D M T I |
| HUMAN | 901 | CGTCAAGAAATGGCTCTAAGTGTTGTT | GATGCTCATGTTCGTGAAAAATTGATTTGG | CTCAGGCAGCAACAAGAAGATATGACTATT |
| RAT | | ---C--- | ---C--A-- | ---T--- G |
| HUMAN | 331 | L L S E V S A A C L | H C E K T L Q Q D D | C R V L A K Q E I |
| HUMAN | 991 | TTGTTGTCAGAGGTTTCTGCAGCCTGCCTC | CACTGTGAAAAGACTTTGCAGCAGGATGAT | TGTAGAGTTGTTGCCAAAACAGGAAATT |
| RAT | | ---C--- ---CC--- ---AA--- ---T-- | ---T--- | ---C--- ---A--- |
| HUMAN | 361 | T R L L T E L Q K Q | Q Q F T E V A D H | I Q L Q A S I P V T |
| HUMAN | 1081 | ACAAGGTTACTGGAAACATTGCAGAAACAG | CAGCAGCAGTTTACAGAAGTTGCAGATCAC | ATTCAGTTGGATGCCAGCATCCCTGTCACT |
| RAT | | ---A-T-A- ---T--- | | ---T-T-A-- |
| HUMAN | 391 | F K D N R V H I G | P K M E I R V T L | G L D G A G K T T I |
| HUMAN | 1171 | TTTACAAAGGATAATCGAGTTCACATTGGA | CCAAAAATGGAAATTCGGGTCGTTACGTTA | GGATTGGATGGTGCTGGAAAAACTACTATC |
| RAT | | ---C--CA-- ---T-T-- | ---C--- ---A--A--C--A-- | ---T--- |
| HUMAN | 421 | L F K L K Q D E F M | Q P I P T I G F N V | E T V E Y K N L K F |
| HUMAN | 1261 | TTGTTTAAGTTAAAACAGGATGAATTCATG | CAGCCCCATTCCAACAATTGGTTTAACGTG | GAAACTGTAGAATATAAAAATCTAAAATTC |
| RAT | | ---C--- ---A--- | ---T-T-- | ---G--C--- |
| HUMAN | 451 | T I W D V G G K H K | L R P L W K H Y Y L | N T Q A V V F V D |
| HUMAN | 1351 | ACTATTTGGGATGTAGGTGGAAAACATCATG | TTAAGACCCCTTTGGAAACATTATTACCTC | AATACTCAAGCTGTTGTTGTTGTAGAT |
| RAT | | ---C---G---A-- | ---T--- | ---A--- ---T--C |
| HUMAN | 481 | S S H R D R I S E A | H S E L A K L L T E | K E L R D A L L L I |

TABLE I-continued

Nucleotide and Protein Alignment of Human and Rat ARD I

| | | | | |
|---|---|---|---|---|
| HUMAN | 1441 | AGCAGTCATAGAGACAGAATTAGTGAAGCA | CACAGCGAACTTGCAAAGTTGTTAACGGAA | AAAGAACTCCGAGATGCTCTGCTCCTGATT |
| RAT | | ----------C---------------- | --------------G--------A--- | -----T-----CT-A---T-- |
| HUMAN | 511 | F  A  N  K  Q  D  V  A  G  A | L  S  V  E  E  I  T  E  L  L | S  L  H  K  L  C  C  G  R  S |
| HUMAN | 1531 | TTTGCTAACAAACAGGATGTTGCTGGAGCA | CTGTCAGTAGAAGAAATCACTGAACTACTC | AGTCTCCATAAATTATGCTGTGGCCGTAGC |
| RAT | | --------------------C-----G- | --T--G--T-----------T-- | -----T-----C--AA--G-- |
| HUMAN | 541 | w  Y  I  Q  G  C  D  A  R  S | G  M  G  L  Y  E  G  L  D  W | L  S  R  Q  L  V  A  A  G  V |
| HUMAN | 1621 | TGGTATATTCAGGGCTGTGATGCTCGAAGT | GGTATGGGACTGTATGAAGGGTTGGACTGG | CTCTCACGGCAACTTGTAGCTGCTGGAGTA |
| RAT | | | | --G--C--------G-----C---- G |
| HUMAN | 571 | L  D  V  A  U | | |
| HUMAN | 1711 | TTGGATGTTGCTGATTTTAAAGGCAGCAG | TTGTTTGAAGTTTTGTGGTTAAAAGTAACT | TTGCACATAAAAAAAAAAAAAAAAATGCA |
| RAT | | ----- | | |
| HUMAN | 1801 | TCTCAAAAGATGGTAATTTAGGATGCATAT | ATATATATATATATATAAAGGAATCTTGGA | TTGGGAATTCAGTACTTGCTTAAAAAAA |
| HUMAN | 1891 | TTTTGTGGCAGAATTAAATTCTAATTGAC | GCAGATTAGATTGAATTAAATAGAAACTTA | TTGAATATACATTCTTTTAAAAGTATATT |
| HUMAN | 1981 | TGTTATTTAAGTTTTTCAGATAATATGTGA | CCAATATACTGGGAAAGAGGTAGTCACAGA | GAAAGGGTAAGTGAAGGTTATCTTCTTCAG |
| HUMAN | 2071 | TGAAAAAGAATAGCCAATTGAGTGCCTAA | TGAGACCTCTGTGTGAAGCAAGTGAAGTAT | AGCTGCTTCTTTTAACCTGCCTTTTCACTG |
| HUMAN | 2161 | AATGTTGGCAGCATTTAGTAGTAGAAATGA | CAGTTGCTTAATGAAATAGAATCCAAACTA | CATATTTGGATAATAGATTACTTTATGTT |
| HUMAN | 2251 | TATGTTCAGAGTAACAGAACACCTTTAAT | GCTAAGAACTATAAGGTACAGAAAATTAAT | ACTTTATATAGTGTTTTATTAACTTCTCC |
| HUMAN | 2341 | TACAGCATTTTGTATAAAACACAATGAGGG | AGTGAAATGTTACCCAATTAGGCTGTCAG | GTTAGTAATAAACTGAACAGTAATAAAACT |
| HUMAN | 2431 | GTGAAGTAATTGGATCTGAATTTATGAAA | GACCCATTTCCAGGACTGAACCTAGGTAG | AGCTCTAAATTGGTCCTTCTATTTTCAAC |
| HUMAN | 2521 | AAATTTAAAGTAATATTTCTTTCTAATATA | ATATTGCATCCTTTGTGGGAATGACTATAG | GTAAAATGTAGTAAGTAACGCAGAACCAGG |
| HUMAN | 2611 | GTTGGCTTATTTAAAAGCTAGTGACCTAA | ATAGAAAGCGAACTTCAAGAGAAGTTGTAA | GTACAGTGGCAAATGCTTATTACTTACTTC |
| HUMAN | 2701 | AAACTGTTTCAAAGAAAAAAAATTCAAAAGT | TTGACAATAAAACTTAAGGCTGTTCATGAG | AAGGCCTTGAAAAGTTACTCTAGAGGAAAA |
| HUMAN | 2791 | ATGTCTAAAGAAAAAAAAAATTCAAAAGT | TTACATTAAATATTCAGTGTGTTGTGAGTAA | TAAAATGTGTGCTCTTTACTGTTTTTCAT |
| HUMAN | 2881 | TTTTAAGAATATTATTATGGAAGCACGAT | TTATTTAAATAGGTACATTGAGACTTTTT | TTTTAATGTTCTGATACATTAGGATGAAGT |
| HUMAN | 2971 | TAAATCTTAAATCTTATTAGTTGAATTGTT | GTAAGGACAGTGATGTCTGGTAACAAGATG | TGACTTTTTGGTAGCACTGTTGTGTTCAT |
| HUMAN | 3061 | TCTTTTCAAATCTATTTTGTTTAAAAACA | ATACAAGTTTTAGAAACAAAGCATTAAAA | AAAAGCCTATCAGTATTATGGCAATATG |
| HUMAN | 3151 | TAAATAATAAATGTAATATTTCATCCTTT | ATTTTTCAAGTAAAAGGTCATGCTGTTACA | GGTGTAGTTTGTTGTGCATAAATAATACTTC |
| HUMAN | 3241 | CGAATTAAATTTATTTAATATTTGACTGATT | TCAATAACTGTGAAATAAAAAGGTGTGT | ATGCTGTGAG |

Table I illustrates the Nucleotide and deduced amino acid sequences of human and rat ARD 1 cDNA. The human ARD 1 deduced amino acid sequence is shown in single-letter code above the nucleotide sequence on the respective codon of the human ARD 1 coding region. Differences in rat ARD nucleotide sequences are shown below the human sequence. The rat ARD 1 sequence is available from positions corresponding to 61 to 1726 of human ARD 1. The human nucleotide sequence shown is SEQ ID NO:1, the rat nucleotide sequence shown is SEQ ID NO:3 and the translated human amino acid sequence shown is SEQ ID NO:2.

An oligonucleotide specific for this sequence (J1R) is shown in Table II and was used to screen a human fetal brain cDNA Lambda ZAP library ($5 \times 10^5$ plaques). Among eight positive clones, #7-3 contained nucleotides 7-1826 and clone #7-8 contained nucleotides 726-3225. In this sequence, about 1200 nucleotides preceded the ARF region without a stop codon in the same reading frame.

dNTPs (1 mM each), bovine serum albumin (0.1 mg/ml), RNasin, 20 units (total volume 20 µl) at 42° C. for 3 hours. TE (10 mM Tris-HCl, pH 7.5, 1 mM EDTA), 1 ml, was added and the mixture was concentrated (Centricon 100). After addition of 2 ml of 0.2×TE, it was concentrated again to 50 µl.

The reverse transcribed products (46 µl) were tailed with terminal deoxynucleotidyl transferase (30 units) at 37° C. for 5 minutes in 0.1M potassium cacodylate, pH 7.2, 2 mM CaCl$_2$, 0.2 mM dithiothreitol, 0.2 mM dATP followed by heat inactivation of the enzyme (65° C., 5 min). The preparation (20 µl) was subjected to PCR (40 cycles: 95° C., 30 seconds; 50° C., 30 seconds; 72° C., 60 seconds) with 200 ng each of primers SALAD and SALADTT (Table III) and 400 ng of primer JK723RII (Table II) in 10 mM Tris-HCl, pH 8.3, 50 mM KCl, 1.5 mM MgCl$_2$, 0.01% gelatin, dNTP, 200 µM each, 0.1% Tween, Taq DNA polymerase, 2.5 units (total volume, 100 µl).

TE (1 ml) was added to the PCR products and the

TABLE II

Oligonucleotides used in the analysis of ARD 1

| Name | Sequence 5'_____3' | |
|---|---|---|
| J1R | AATGGGCTGCATGAATTCATCCTGTTTTAA | (SEQ ID NO:3) |
| | complementary to bases 1270 to 1299 of human ARD 1. | |
| JK721RC | CCTCCTTCAATGTGCTGCACAATTCC | (SEQ ID NO:4) |
| | complementary to bases 757 to 782 of human ARD 1. | |
| JK723RII | TGAGTAACTTGAGAACACTC | (SEQ ID NO:5) |
| | complementary to bases 445 to 464 of human ARD 1. | |
| JK728R | TGCCCTGCCGGCCACTGTCTACTCCCGCTCCGAGCTTGTTTA | (SEQ ID NO:6) |
| | complementary to bases 17 to 58 of human ARD 1. | |
| JKNOT | GACTAGTTCTAGATCGCGAGCGGCCGCCCTTCACCTAGGTCTGTTACTTGTCG | (SEQ ID NO:7) |
| | complementary to bases 226 to 248 of human ARD 1 with 30 bases added at 5' end to introduce NotI site. | |
| JK8EX | GGCCTGGTTCCGCGGATGGCTACCCTGGTTGTA | (SEQ ID NO:8) |
| | bases 1 to 18 of human ARD 1 with 15 bases added at 5' end to introduce ligation-independent cloning site. | |
| JK3EX | GGCCTGGTTCCGCGGATGGAAATTCGGGTC | (SEQ ID NO:9) |
| | bases 1207 to 1221 of human ARD 1 with 15 bases added at 5' end to introduce ligation-independent cloning site. | |
| JKEXR | CTGCGCCTCGCTCCTCAAGCAACATCCAA | (SEQ ID NO:10) |
| | complementary to bases 1711 to 1725 of human ARD I with 14 bases added at 5' end to introduce ligation-independent cloning site. | |
| JK5EXR | CTGCGCCTCGCTCCTTTTGGTCCAATGTG | (SEQ ID NO:11) |
| | complementary to bases 1192 to 1206 of human ARD 1 with 14 bases added at 5' end to introduce ligation-independent cloning site. | |

To further characterize the 5'-terminus of this cDNA, 5'-RACE was carried with the poly(A)+ RNA from IMR-32 human neuroblastoma cells.

Experiment 2
5'-RACE with IMR-32 Poly(A)+ RNA

Poly(A)+ RNA (5 µg) from IMR-32 human neuroblastoma cells was reverse-transcribed with the primer JK721RC, as shown in Table II (100 ng) by AMV reverse transcriptase (20 units) in 50 mM Tris-HCl, pH 8.3, 7 mM MgCl$_2$, 40 mM KCl, 1 mM dithiothreitol, mixture was concentrated (Centricon 100). TE (2 ml) was added followed by concentration to 30 µl and transfer of a sample (1 µl) to a second PCR amplification (40 cycles: 95° C., 30 seconds; 50° C., 30 seconds; 72° C., 30 seconds) with 400 ng each of primers SALAD (Table III) and JKNOT (Table II). Preparations were digested with NotI and SalI, ligated into plasmid pSPORT1, and used to transform competent DH5α cells, which were then grown on LB/agar plates containing ampicillin, 100 µg/ml.

TABLE III

Oligonucleotides used in the analysis of ARD 1

| Name | Sequence, 5'-3' |
|---|---|
| RA4CF | ATGGGCCTCACCAT |
| | (SEQ ID NO:12) |
| | Bases 1 to 14 of rat ARF 4. |
| HARF4-codAR | TCTCACTGATGGCCATAGCA |
| | (SEQ ID NO:13) |
| | Complementary to bases 396 to 415 of rat and human ARF 4 cDNA. |
| HRA4CR | TCATTTGACAGCCA |
| | (SEQ ID NO:14) |
| | Complementary to bases 514 to 527 of rat and human ARF 4 |

TABLE III-continued

Oligonucleotides used in the analysis of ARD 1

| Name | Sequence, 5'-3' |
|---|---|
| REKNOT | cDNA.<br>GACTAGTTCTACATCGCGAGCGGCCGCCCTGGATATCTAACCAAGGACAT<br>(SEQ ID NO.:34)<br>Bases 552 to 571 of rat ARF 4 with 40 bases added at 5'-end to introduce a NotI site. |
| RDK1CF | TTGATAGAATTGGTCTAGGCTTGTTACAAC<br>(SEQ ID NO:15)<br>Bases 574 to 603 of rat ARF 4 CDNA (just after stop codon). |
| RDK1R | GTTGTAACAAGCCTAGACCAATTCTATCAA<br>(SEQ ID NO:16)<br>Complementary to RDK1CF |
| RDK3R | GGCTAAACAGCAACATTGTTCTTGGTAAACAATAATTGGCAACAAAAC<br>(SEQ ID NO:17)<br>Complementary to bases 677 to 724 of rat ARF 4 CDNA (after first polyadenylation signal). |
| RDK4R | TCAGTGAGTTCCAAGGGGGTAACTTTAAAACATTATTGGTGTGGGCTC<br>(SEQ ID NO:18)<br>Complementary to bases 855 to 902 of rat ARF 4 CDNA (after second polyadenylation signal). |
| RAKRIIa | TGGAATCGGAACTTCCAGATCCTCATCGTCCGAGTCCGATTCACTCTG<br>(SEQ ID NO:19)<br>Complementary to bases 127 to 174 of rat RIIαCDNA (regulatory subunit of cAMP-dependent protein kinase) (30). |
| SALADTT | CTCGTGGACGATGTTGCTGTCGACCCACGCGTCCG(T)20<br>(SEQ ID NO:20)<br>Oligo(dT) with 35 bases containing a SalI site at 5' -end. |
| SALAD | CTCGTGGACGATGTTGCTGTCGACCCACGCGTCCG<br>(SEQ ID NO:21) |
| R2SCR | TTTGTACAAGATCGTCGTTTTGCCAGCTGCATCTAAGCC<br>(SEQ ID NO:22)<br>Used for screening. |
| RDK5NOT | GACTAGTTCTAGATCGCGAGCGGCCGCCACCACCGCTATGGGC<br>(SEQ ID NO:23)<br>Bases −12 to 6 with 25 bases added to introduce a NotI site. |
| RDKSAL1 | CTCGTGGACGATGTGCTGGTCGACAGCTGCCCAAACCGTCTCAG<br>(SEQ ID NO:24)<br>Complementary to bases 638 to 655 with 26 bases added at 5'-end to introduce SalI and PuuII sites. |
| RDKSAL2 | CTCGTGGACGATGTGCTGGTCGACGTTAACACTCAAAACAGATTT<br>(SEQ ID NO:25)<br>Complementary to bases 833 to 850 with 27 bases added at 5'-end to introduce SalI and PuuII sites. |
| RDKSAL3 | CTCGTGGACGATGTGCTGGTCGACTCGAAAAATCATTTTATTAGGAATAATTCCA<br>(SEQ ID NO:26)<br>Complementary to bases 1362 to 1389 with 27 baseo added at 5' -end to introduce SalI and TagI sites. |

Following transfection of the reverse transcribed, PCR amplified sequences into competent DH5α cells, we isolated clones corresponding to ARD 1.

Experiment 3

Isolation of ARD 1 from Human and Rat

Colonies were screened with probe JK728R (Table II) that had been labeled with [α-$^{32}$P]dATP and terminal deoxynucleotidyl transferase. Positive clones (33) were selected and grown in LB containing ampicillin, 100 μg/ml. Plasmid DNA was purified and digested with Sal I and Not I. Longer inserts (~350 bp) from seven clones were sequenced. A consensus sequence of the 5' -terminal sequences of four are shown in Table I; three clones had shorter inserts.

Four clones with the longest inserts had an initiation codon ATG accompanied by A at −3 and G at position 4. This sequence is believed favorable for translation initiation (Kozak, et al. *J. Cell. Biol.* 108: 229-241 (1989)). The putative open reading frame of this gene, termed ARD 1, consisted of 1722 nucleotides encoding a protein of 574 amino acids with an ARF related domain at the carboxyl terminus. We anticipated that human and rat ARD 1 were likely similar, so we isolated clones corresponding to rat ARD 1.

A rat brain Lambda ZAP II library (6×10$^5$ plaques) was screened with an oligonucleotide R2SCR (TABLE III) that yielded clone 2$^a$ containing an insert that corresponded to nucleotides 61-1973 of human ARD 1. A comparison of the rat and human sequences is provided in Table I.

Nucleotide and deduced amine acid sequences of ARD 1 coding regions from rat and human are 92% and 98% identical, respectively, without any gaps. The nucleotide sequence of the ARF domain of human ARD 1 is 60-66% identical to those of the mammalian ARFs; the deduced amino acid sequences are 55-60% identical or 69-72% similar including conservative placements (Table IV).

TABLE IV

Comparison of nucleotide and deduced amino acid sequences of the ARF domain of human ARD 1 (172 amino acids) to those of mammalian ARFs

| Mammalian ARF | Percentage identity to hARD 1 | |
|---|---|---|
| | Nucleotides | Amino acids |
| hARF 1 | 62 | 59 (71)* |

TABLE IV-continued
Comparison of nucleotide and deduced amino acid sequences of the ARF domain of human ARD 1 (172 amino acids) to those of mammalian ARFs

| Mammalian ARF | Percentage identity to hARD 1 | |
|---|---|---|
| | Nucleotides | Amino acids |
| hARF 2 | 66 | 59 (72) |
| hARF 3 | 65 | 60 (72) |
| hARF 4 | 66 | 59 (72) |
| hARF 5 | 62 | 56 (72) |
| hARF 6 | 60 | 55 (69) |

*identical plus conservative replacements
Programs used were PC/Gene FASTSCAN for nucleotide sequence and PC/Gene PALIGN (open gap cost, 1; unit gap cost, 1) for amino acid sequence Some of the regions common to ARFs thus far identified that are believed to be involved in guanine nucleotide binding and TP hydrolysis are also conserved in ARD 1 (FIG. 1), i.e., GLDGAGK (411–417), DVGG (454–457), and NKQD (513–516); CAT, however, is missing and replaced with DAR ( 547–549 ) .

To analyze the expression of ARD 1, we probed Northern blots of RNA from various tissues.

Experiment 4
Northern Analysis of ARD 1

Poly(A)+ RNA was isolated from total RNA (Chomyczynski, et al. *Anal. Biochem.* 162: 156–159 (1987)) using oligo(dT) chromatography (Chirgwin, et al. *Biochemistry* 18: 5294–5299 (1979)). Poly(A)+ RNA (5 µg) was then fractionated by electrophoresis in 1.2% agarose/formaldehyde gels and transferred to Nytran.

Prehybridization and hybridization were carried out at 42° C. in hybridizaton buffer of 5× SSC (1× =0.15M NaCl, 0.015M sodium citrate, pH 7.0), 5× Denhardt's solution (1× =0.02% Ficoll, 0.02% polyvinylpyrrolidone, 0.02% bovine serum albumin), 10 mM Tris-HCl, pH 7.4, 0.1% SDS, 10% dextran sulfate, denatured salmon sperm DNA, 0.1 mg/ml, 40% formamide. Filters were washed at 55° C. once with 2× SSC, 0.5% SDS and twice with 0.5× SSC, 0.5% SDS. Filters were exposed to Kodak XAR film at −80° C. with an intensifying screen. Human ARF 1 coding region cDNA was prepared as described by Bobak et al. (*Proc. Natl. Acad. Sci.* (USA) 86: 6101–6105 (1989)). Human ARD 1 coding region cDNA was generated by PCR as described above.

Figure 3:
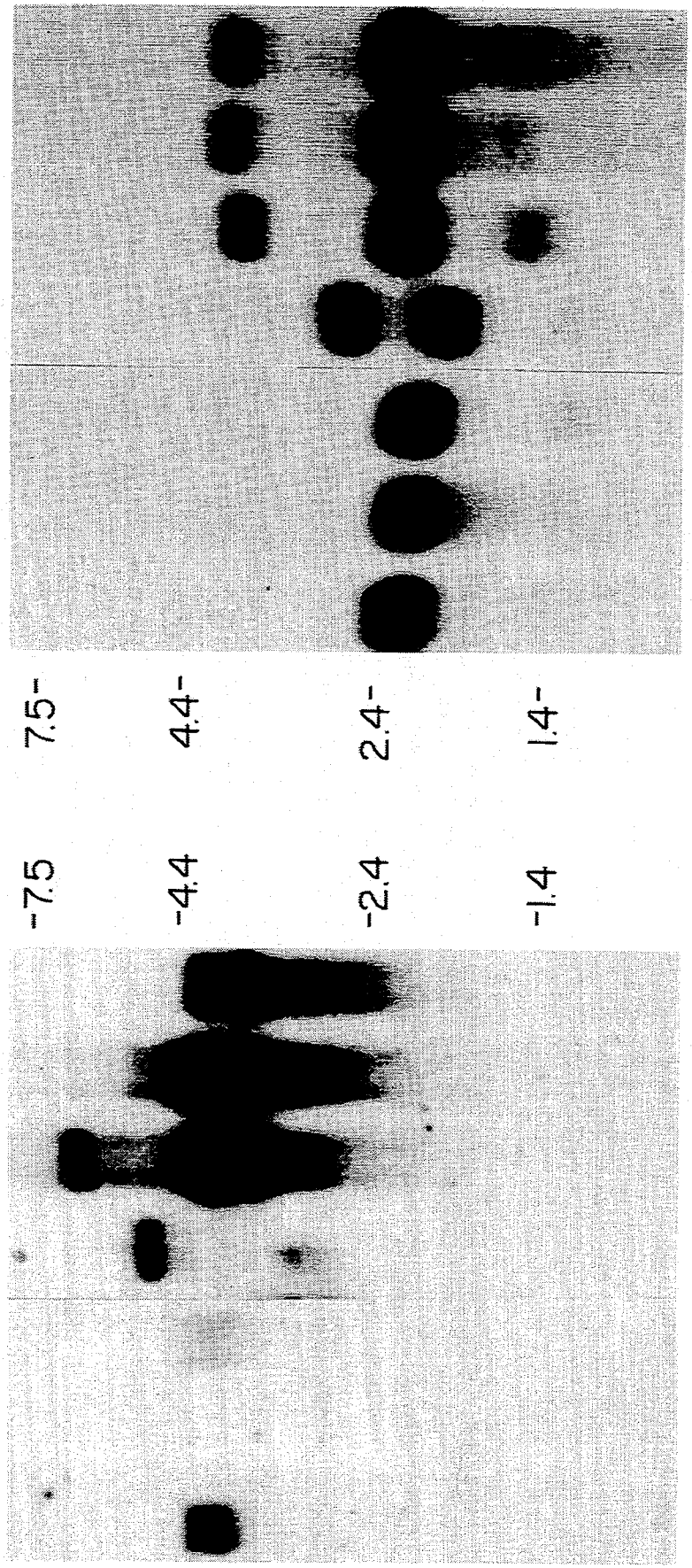
FIG. 3 is a copy of a Northern blot illustrating the hybridization of poly (A)+ RNA from different species with ARD 1 coding region cDNA. Poly(A)+ RNA from human fibroblasts (FB), HL-60 (HL), and IMR-32 (IM) cells and brain from chicken (Ch), rabbit (Rb), mouse (Mo), and rat (Rt) was hybridized with human ARD 1 coding region cDNA FIG. 3A or human ARF 1 coding region cDNA FIG. 3B as described below. Positions of standards (kb) are indicated.

An ARD 1 coding region cDNA clone hybridized with 4.2-kb and 3.7-kb mRNAs from all rat tissues examined (FIG. 2). This probe also hybridized with bands of similar size in poly(A)+ RNA from mouse and rabbit brain and human fibroblasts. Poly(A)+ RNA from IMR-32 cells, however, hybridized very weakly while RNA from undifferentiated HL-60 cells did not hybridize detectably. However, all samples of poly(A)+ RNA hybridized essentially equally well with a human ARF 1 coding region cDNA (FIG. 3).

To assess the ability of ARD 1 to enhance cholera toxin ADP-ribosyltransferase, recombinant GST-ARD 1 fusion proteins were prepared.

Experiment 5
Expression of the Fusion Proteins

Three ARD 1 fusion proteins with glutathione S-transferase (GST) were synthesized employing a ligation-independent cloning method (Haun et al. *Gene* 112: 39–43 (1992)), using clone #7-3 and oligonucleotide primers as indicated in Table II. For GST-p8 (containing the entire sequence from Met[1] to Ala [574]), oligonucleotides JK8EX and JKEXR (Table II) were used. For GST-p3 (the ARF domain from Met[403] to Ala[574]), oligonucleotides JK3EX and JKEXR (Table II) were used. For GST-p5 (the non-ARF sequence from Met[1] to Lys[402]) oligonucleotides JK8EX and JK5EXR (Table II) were used. The fusion proteins were purified with glutathione-agarose by well known methods as described in Smith et al. *(Gene* 67: 31–40 (1988)). To test the ability of each fusion protien to bind GTP we performed the following experiments.

Experiment 6
GTP-binding Assay with Recombinant ARD1

Fragment p3 (2µg), p8 (4 µg), and sARF II (0.2 µg) were subjected to electrophoresis in 4–20% polyacrylamide gels with SDS and transferred to nitrocellulose. The membrane was incubated in 50 mM Tris-HCl, pH 7.5, 150 mM NAcl, 2 mM dithiothreitol, 2.5 mM EDTA, soybean trypsin inhibitor, 10 µg/ml, 0.5 mM PMSF, 0.3% bovine serum albumin, 0.#% Tween 20 (binding buffer) at room temperature for 2 h, transferred to fresh binding buffer containing 8 mM MgCl$_2$ and [α-$^{32}$P]GTP (800 Ci/mmol), 1 µCi/ml, for 2 h, washed three times with binding buffer for 5 min, briefly dried, and exposed to Kodak XAR film at −80° C. overnight with intensifying screen.

The affinity of GST-p3 for GTP was apparently lower than that of GST-p8, p8 or sARF II. GTP concentrations required for half-maximal activation were less than 10 µM with GST-p8, p8, and sARF II and ~50 µM with GST-p3.

Figure 4:
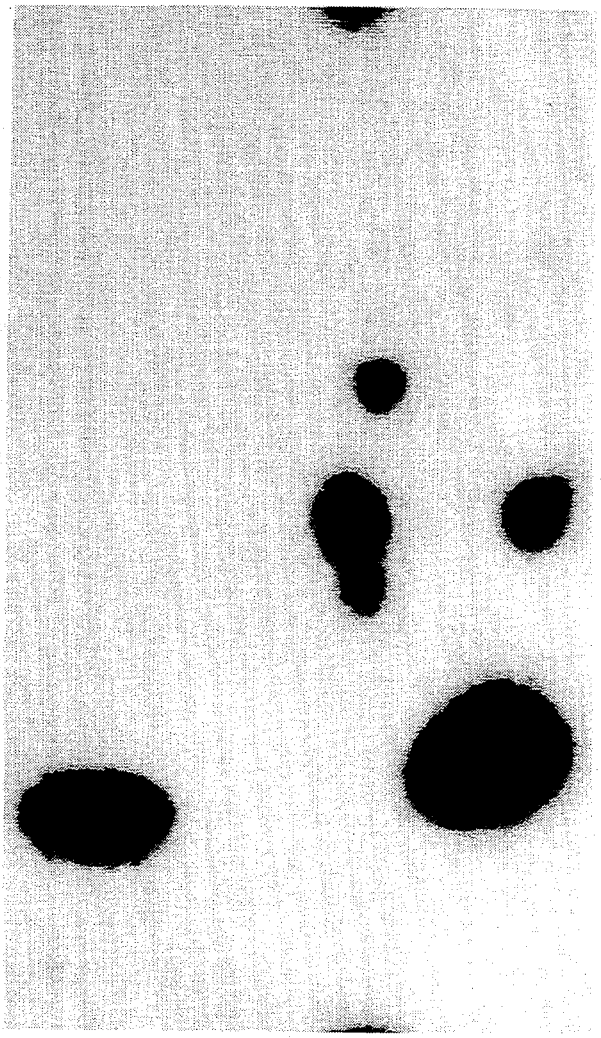
FIG. 4 is copy of a protein gel illustrating the binding of GTP to recombinant ARD 1. p3 (2 µg), p8 (Mg) and sARF II (0.2 µg) were subjected to 4–20% SDS-polyacrylamide gel electrophoresis, and transferred to nitrocellulose membrane. [$\alpha$-$^{32}$P] GTP binding was carried out in the presence of 0.3% Tween 20 as described below.

Through the use of specific primers, as discussed above, GST-p8 contained the entire ARD 1 protein, GST-p3 contained the carboxy-terminal ARF domain, and GST-p5 contained the non-ARF domain. The recombinant ARF domain of ARD 1 bound GTP after SDS-PAGE and transfer to nitrocellulose membrane, whereas p8, which contained the entire sequence of ARD 1, exhibited no detectable binding (FIG. 4). It is possible that the longer p8 protein was unable to bind GTP due to a conformational change when attached to the nitrocellulose membrane. The shorter GST-p3 protein, however, was able to bind GTP even after attachment to the nitrocellulose membrane.

Figure 5:
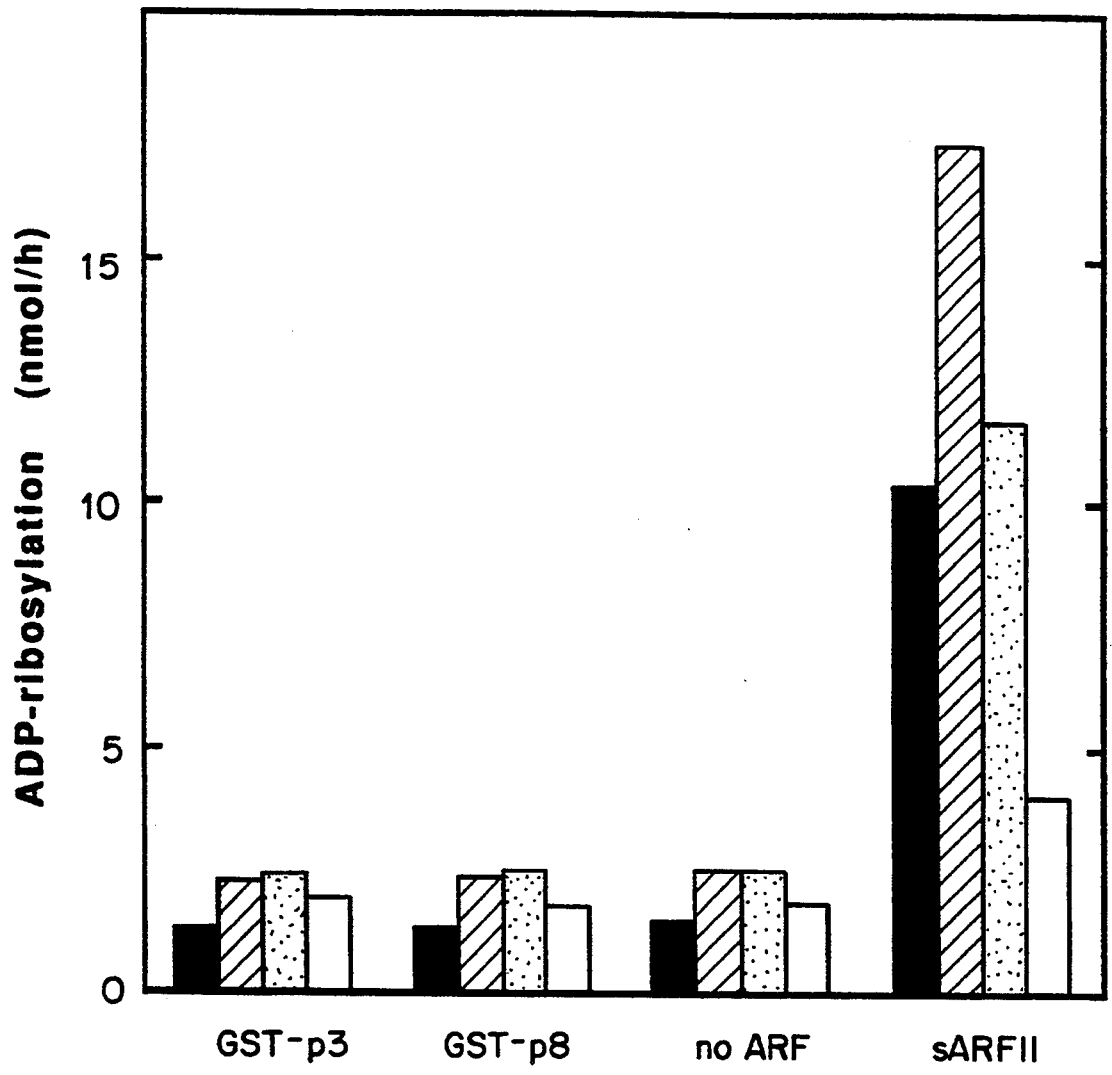
FIG. 5 is a bar graph illustrating the effects of lipids/detergents on ARF activity. Cholera toxin-catalyzed ADP-ribosylation of agmatine was assayed in the presence of GST-p3 (4 µg), GST-p8 (8 µg), sARF II (2 µg) or no ARF as described below. The lipids/detergents used were 0.003% SDS ( ), 1 mg/ml cardiolipin (striped rectangles), 3 mM DMPC/0.4% cholate (dotted rectangles) or 0.4% cholate (hollow rectangles).

As shown in FIG. 5, ARD 1 fusion proteins did not stimulate ADP-ribosylation by cholera toxin in the presence of SDS, DMPC/cholate, or cardiolipin, which to differing degrees enhanced the activity of sARF II. In the presence of 0.3% Tween 20, however, recombinant ARD 1, p8, and GST-p8 increased the toxin ADP-ribosyltransferase in a dose-dependent manner (FIG. 6).

Experiment 7
NAD/Agmatine ADP-ribosylation Assay

Stimulation of cholera toxin-catalyzed ADP-ribosylation of agmatine was assayed to evaluate ARF activity of the recombinant proteins. Reaction mixtures contained 50 mM potassium phosphate (pH 7.5), 4 mM MgCl$_2$, 30 mM dithiothreitol, ovalbumin (0.3 mg/ml), 0.2 mM [adenine-$^{14}$C]NAD (0.05 µCi), 20 mM agmatine, 0.3% Tween 20, cholera toxin (0.5 µg), 1 mM GTP or 0.1 mM GDPβS, and the indicated amount of sARF II or recombinant protein (total volume 200 µl ). After incubation at 30° C. for 1 hour, duplicate samples (80 µl ) were transferred to columns of AG1-X2, equilibrated with water and eluted five times with five 1 ml washes of water. The eluate, containing [$^{14}$C]ADP-ribosylagmatine, was collected for radioassay.

Figure 6:
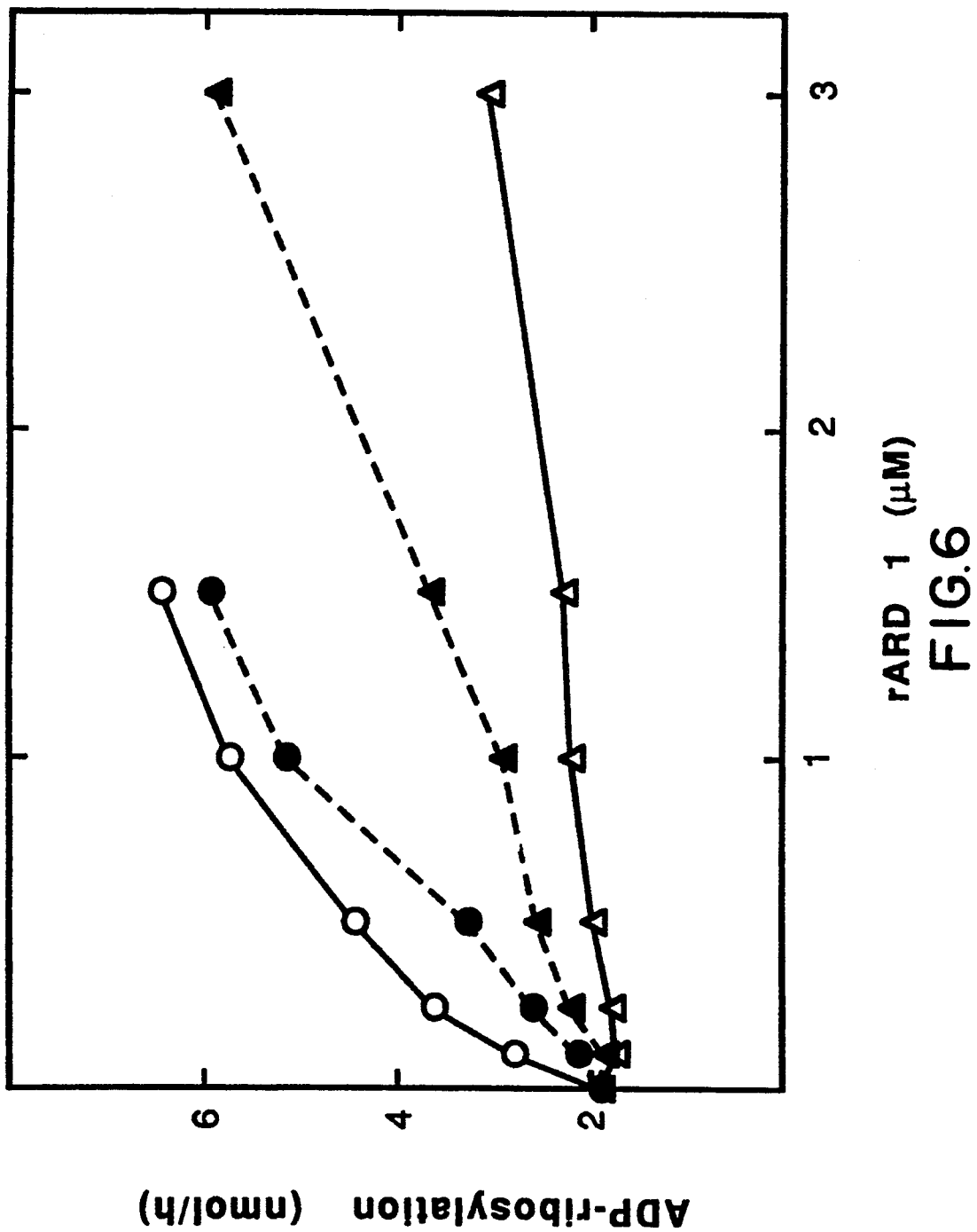
FIG. 6 is a line graph showing the effect of the increasing concentration of ARD 1 on cholera toxin-catalyzed ADP-ribosylation. Cholera toxin-catalyzed ADP-ribosylation of agmatine was assayed in the presence of indicated concentrations of recombinant ARD 1; GST-p8 ( , p8 (o), GST-p3 , p3 (Δ).
Figure 7:
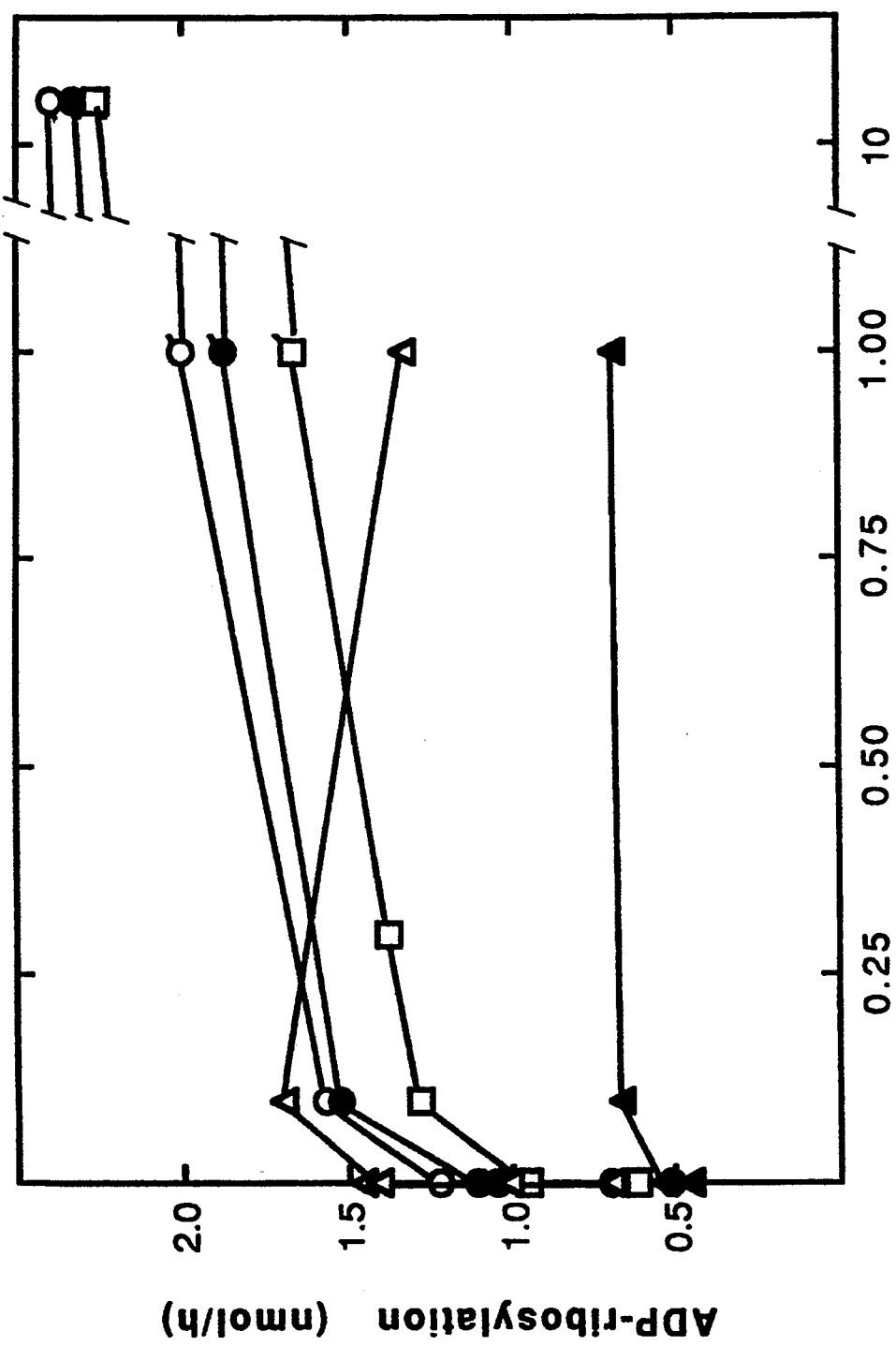
FIG. 7 is a line graph illustrating the effect of GTP concentration on ARF activity in the presence of 0.3% Tween 20. Cholera toxin-catalyzed ADP-ribosylation of agmatine with 20 µg of GST-p8 (o), 14 µg of p8 ( ), 25 µg of GST-p3 (hollow box), 2 µg of sARF II (Δ) or no ARF ( ) was assayed in the presence of indicated concentration of GTP. The activities without GTP (0.1 mM GDP$\beta$S) was 0.51 nmol/h (GST-p8), 0.64 nmol/h (p8), 0.61 nmol/h (GST-p3), 0.70 nmol/h (sARF II) and 0.46 nmol/h (no ARF).

In the presence of 0.3% Tween 20, recombinant ARD 1, p8, and GST-p8, increased the toxin ADP-ribosyltransferase in a dose-dependent manner (FIG. 6). The activity of GST-p3 was clearly less, whereas p3 had little if any activity. Maximal activation seemed to be similar; half-maximal activation was achieved with 0.5 μM p8, 0.75 μM GST-p8 and 2 μM GST-3 (FIG. 6). sARF II also stimulated the toxin transferase activity in Tween 20 (FIG. 7), although to a lesser extent than it did in the presence of SDS, DMPC/cholate, or cardiolipin (FIG. 5). GST-p5, p5, or GST did not enhance cholera toxin activity (data not shown). Activity of the recombinant ARD 1 proteins was dependent on GTP (FIG. 7), as is the case with the ARFs.

Monoclonal antibodies against ARD 1 could be useful for the reasons cited above and can be produced by the following method.

Example 8

Production of Monoclonal Antibodies

Monoclonal antibodies to ARD 1 are generated using conventional techniques, such as those disclosed in Basic Methods in Molecular Biology 351 (Davis, et al., 1986). Briefly, ten mice are each innoculated intraperitoneally with 500 μg of human ARD 1 antigen in a 1:1 emulsion with complete Freund's adjuvant. Thereafter, the mice are boosted with three additional injections at 15 day intervals of the same amount of antigen in a 1:1 emulsion with incomplete Freund's adjuvant. Three days following the third booster injection, the mice are sacrificed and the spleens are harvested. The spleen cells are separated and fused with myeloma cells according to the method of Kohler and Milstein by combining the spleen cells with mouse myeloma cells in a ratio of 6:1, centrifuging at 4000×g for 10 minutes, loosening the pellet with 1 ml 50% PEG, adding 9 ml DMEM, centrifuging again at 600×g for 10 minutes, and growing the cells in HAT in a 96 well tissue culture plate. Positive clones are expanded and the supernatant is screened against ARD 1.

Once antibodies against ARD 1 have been produced they can be used in assays such as an ELISA, as discussed below.

Example 9

ELISA for Antibodies Against ARD 1

A sample from either an organism or a hybridoma is screened for the presence of ARD 1 using a conventional ELISA. Briefly, 200 μl of purified ARD 1 is added to a well of a microtiter plate and is permitted to bind to the plastic plate for 48 hours at 4° C. The well is washed with 0.15M NaCl containing 0.05% Tween 20. Sample is mixed with PBS containing 0.05% Tween 20 and BSA at 0.1mg/ml, and aliquots are added to the treated plastic well. Plates are incubated for 1 hr at room temperature, washed, and 200μl of 1:400 goat-antimouse IgG conjugated to alkaline phosphatase is added. After a 1 hour incubation, the well is again washed, after which 200 μl of p-nitrophenyl phosphate is added. Color development takes about one hour; development of color indicates a positive assay.

From the above data it is tempting to speculate that ARD 1 is related to a new family of larger ARF proteins and representing larger GTP-binding proteins that contain a domain with ARF structure and function as well as another domain whose function is at present unknown.

It can be appreciated that the previous experiments are only illustrative of specific embodiments of the present invention. This invention should not be limited to those embodiments disclosed by the aforementioned experiments, but only by the following claims.

---

What is claimed is:

1. An isolated polynucleotide encoding the ARD1 protein, said polynucleotide having the nucleotide sequence of SEQ ID NO:1.

2. A nucleic acid expression vector, said expression vector having the nucleotide sequence of SEQ ID NO:1 operably linked to a promoter.

3. A cell transfected with the expression vector of claim 2.

4. An isolated polynucleotide encoding the ARD 1 protein, said ARD1 protein having the amino acid sequence of SEQ ID NO:2.

5. The isolated polynucleotide of claim 4, wherein said polynucleotide is operably linked to a heterologous promoter.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 3312 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..1725

( x i ) SEQUENCE DESCRIPTION: SEQ ID NO:1:

```
ATG  GCT  ACC  CTG  GTT  GTA  AAC  AAG  CTC  GGA  GCG  GGA  GTA  GAC  AGT  GGC        48
Met  Ala  Thr  Leu  Val  Val  Asn  Lys  Leu  Gly  Ala  Gly  Val  Asp  Ser  Gly
 1              5                   10                  15

CGG  CAG  GGC  AGC  CGG  GGG  ACA  GCT  GTA  GTG  AAG  GTG  CTA  GAG  TGT  GGA        96
Arg  Gln  Gly  Ser  Arg  Gly  Thr  Ala  Val  Val  Lys  Val  Leu  Glu  Cys  Gly
             20                  25                  30
```

-continued

| | | | | | | | | | | | | | | | | |
|---|---|---|---|---|---|---|---|---|---|---|---|---|---|---|---|---|
| GTT | TGT | GAA | GAT | GTC | TTT | TCT | TTG | CAA | GGA | GAC | AAA | GTT | CCC | CGT | CTT | 144 |
| Val | Cys | Glu | Asp | Val | Phe | Ser | Leu | Gln | Gly | Asp | Lys | Val | Pro | Arg | Leu | |
| | | 35 | | | | | 40 | | | | | 45 | | | | |
| TTG | CTT | TGT | GGC | CAT | ACC | GTC | TGT | CAT | GAC | TGT | CTC | ACT | CGC | CTA | CCT | 192 |
| Leu | Leu | Cys | Gly | His | Thr | Val | Cys | His | Asp | Cys | Leu | Thr | Arg | Leu | Pro | |
| | 50 | | | | | 55 | | | | | 60 | | | | | |
| CTT | CAT | GGA | AGA | GCA | ATC | CGT | TGC | CCA | TTT | GAT | CGA | CAA | GTA | ACA | GAC | 240 |
| Leu | His | Gly | Arg | Ala | Ile | Arg | Cys | Pro | Phe | Asp | Arg | Gln | Val | Thr | Asp | |
| 65 | | | | | 70 | | | | | 75 | | | | | 80 | |
| CTA | GGT | GAT | TCA | GGT | GTC | TGG | GGA | TTG | AAA | AAA | AAT | TTT | GCT | TTA | TTG | 288 |
| Leu | Gly | Asp | Ser | Gly | Val | Trp | Gly | Leu | Lys | Lys | Asn | Phe | Ala | Leu | Leu | |
| | | | | 85 | | | | | 90 | | | | | 95 | | |
| GAG | CTT | TTG | GAA | CGA | CTG | CAG | AAT | GGG | CCT | ATT | GGT | CAG | TAT | GGA | GCT | 336 |
| Glu | Leu | Leu | Glu | Arg | Leu | Gln | Asn | Gly | Pro | Ile | Gly | Gln | Tyr | Gly | Ala | |
| | | | 100 | | | | | 105 | | | | | 110 | | | |
| GCA | GAA | GAA | TCC | ATT | GGG | ATA | TCT | GGA | GAG | AGC | ATC | ATT | CGT | TGT | GAT | 384 |
| Ala | Glu | Glu | Ser | Ile | Gly | Ile | Ser | Gly | Glu | Ser | Ile | Ile | Arg | Cys | Asp | |
| | | 115 | | | | | 120 | | | | | 125 | | | | |
| GAA | GAT | GAA | GCT | CAC | CTT | GCC | TCT | GTA | TAT | TGC | ACT | GTG | TGT | GCA | ACT | 432 |
| Glu | Asp | Glu | Ala | His | Leu | Ala | Ser | Val | Tyr | Cys | Thr | Val | Cys | Ala | Thr | |
| | 130 | | | | | 135 | | | | | 140 | | | | | |
| CAT | TTG | TGC | TCT | GAG | TGT | TCT | CAA | GTT | ACT | CAT | TCT | ACA | AAG | ACA | TTA | 480 |
| His | Leu | Cys | Ser | Glu | Cys | Ser | Gln | Val | Thr | His | Ser | Thr | Lys | Thr | Leu | |
| 145 | | | | | 150 | | | | | 155 | | | | | 160 | |
| GCA | AAG | CAC | AGG | CGA | GTT | CCT | CTA | GCT | GAT | AAA | CCT | CAT | GAG | AAA | ACT | 528 |
| Ala | Lys | His | Arg | Arg | Val | Pro | Leu | Ala | Asp | Lys | Pro | His | Glu | Lys | Thr | |
| | | | | 165 | | | | | 170 | | | | | 175 | | |
| ATG | TGC | TCT | CAG | CAC | CAG | GTG | CAT | GCC | ATT | GAG | TTT | GTT | TGC | TTG | GAA | 576 |
| Met | Cys | Ser | Gln | His | Gln | Val | His | Ala | Ile | Glu | Phe | Val | Cys | Leu | Glu | |
| | | | 180 | | | | | 185 | | | | | 190 | | | |
| GAA | GGT | TGT | CAA | ACT | AGC | CCA | CTC | ATG | TGC | TGT | GTC | TGC | AAA | GAA | TAT | 624 |
| Glu | Gly | Cys | Gln | Thr | Ser | Pro | Leu | Met | Cys | Cys | Val | Cys | Lys | Glu | Tyr | |
| | | 195 | | | | | 200 | | | | | 205 | | | | |
| GGA | AAA | CAC | CAG | GGT | CAC | AAG | CAT | TCA | GTA | TTG | GAA | CCA | GAA | GCT | AAT | 672 |
| Gly | Lys | His | Gln | Gly | His | Lys | His | Ser | Val | Leu | Glu | Pro | Glu | Ala | Asn | |
| | 210 | | | | | 215 | | | | | 220 | | | | | |
| CAG | ATC | CGA | GCA | TCA | ATT | TTA | GAT | ATG | GCT | CAC | TGC | ATA | CGG | ACC | TTC | 720 |
| Gln | Ile | Arg | Ala | Ser | Ile | Leu | Asp | Met | Ala | His | Cys | Ile | Arg | Thr | Phe | |
| 225 | | | | | 230 | | | | | 235 | | | | | 240 | |
| ACA | GAG | GAA | ATC | TCA | GAT | TAT | TCC | AGA | AAA | TTA | GTT | GGA | ATT | GTG | CAG | 768 |
| Thr | Glu | Glu | Ile | Ser | Asp | Tyr | Ser | Arg | Lys | Leu | Val | Gly | Ile | Val | Gln | |
| | | | | 245 | | | | | 250 | | | | | 255 | | |
| CAC | ATT | GAA | GGA | GGA | GAA | CAA | ATC | GTG | GAA | GAT | GGA | ATT | GGA | ATG | GCT | 816 |
| His | Ile | Glu | Gly | Gly | Glu | Gln | Ile | Val | Glu | Asp | Gly | Ile | Gly | Met | Ala | |
| | | | 260 | | | | | 265 | | | | | 270 | | | |
| CAC | ACA | GAA | CAT | GTA | CCA | GGG | ACT | GCA | GAG | AAT | GCC | CGG | TCA | TGT | ATT | 864 |
| His | Thr | Glu | His | Val | Pro | Gly | Thr | Ala | Glu | Asn | Ala | Arg | Ser | Cys | Ile | |
| | | 275 | | | | | 280 | | | | | 285 | | | | |
| CGA | GCT | TAT | TTT | TAT | GAT | CTA | CAT | GAA | ACT | CTG | TGT | CGT | CAA | GAA | GAA | 912 |
| Arg | Ala | Tyr | Phe | Tyr | Asp | Leu | His | Glu | Thr | Leu | Cys | Arg | Gln | Glu | Glu | |
| | 290 | | | | | 295 | | | | | 300 | | | | | |
| ATG | GCT | CTA | AGT | GTT | GTT | GAT | GCT | CAT | GTT | CGT | GAA | AAA | TTG | ATT | TGG | 960 |
| Met | Ala | Leu | Ser | Val | Val | Asp | Ala | His | Val | Arg | Glu | Lys | Leu | Ile | Trp | |
| 305 | | | | | 310 | | | | | 315 | | | | | 320 | |
| CTC | AGG | CAG | CAA | CAA | GAA | GAT | ATG | ACT | ATT | TTG | TTG | TCA | GAG | GTT | TCT | 1008 |
| Leu | Arg | Gln | Gln | Gln | Glu | Asp | Met | Thr | Ile | Leu | Leu | Ser | Glu | Val | Ser | |
| | | | | 325 | | | | | 330 | | | | | 335 | | |
| GCA | GCC | TGC | CTC | CAC | TGT | GAA | AAG | ACT | TTG | CAG | CAG | GAT | GAT | TGT | AGA | 1056 |
| Ala | Ala | Cys | Leu | His | Cys | Glu | Lys | Thr | Leu | Gln | Gln | Asp | Asp | Cys | Arg | |
| | | | 340 | | | | | 345 | | | | | 350 | | | |
| GTT | GTC | TTG | GCA | AAA | CAG | GAA | ATT | ACA | AGG | TTA | CTG | GAA | ACA | TTG | CAG | 1104 |
| Val | Val | Leu | Ala | Lys | Gln | Glu | Ile | Thr | Arg | Leu | Leu | Glu | Thr | Leu | Gln | |

-continued

|     |     |     |     |     | 355 |     |     |     |     |     | 360 |     |     |     |     | 365 |     |      |
| --- | --- | --- | --- | --- | --- | --- | --- | --- | --- | --- | --- | --- | --- | --- | --- | --- | --- | ---- |

```
AAA CAG CAG CAG CAG TTT ACA GAA GTT GCA GAT CAC ATT CAG TTG GAT    1152
Lys Gln Gln Gln Gln Phe Thr Glu Val Ala Asp His Ile Gln Leu Asp
    370             375                 380

GCC AGC ATC CCT GTC ACT TTT ACA AAG GAT AAT CGA GTT CAC ATT GGA    1200
Ala Ser Ile Pro Val Thr Phe Thr Lys Asp Asn Arg Val His Ile Gly
385             390                 395                 400

CCA AAA ATG GAA ATT CGG GTC GTT ACG TTA GGA TTG GAT GGT GCT GGA    1248
Pro Lys Met Glu Ile Arg Val Val Thr Leu Gly Leu Asp Gly Ala Gly
                405                 410                 415

AAA ACT ACT ATC TTG TTT AAG TTA AAA CAG GAT GAA TTC ATG CAG CCC    1296
Lys Thr Thr Ile Leu Phe Lys Leu Lys Gln Asp Glu Phe Met Gln Pro
            420                 425                 430

ATT CCA ACA ATT GGT TTT AAC GTG GAA ACT GTA GAA TAT AAA AAT CTA    1344
Ile Pro Thr Ile Gly Phe Asn Val Glu Thr Val Glu Tyr Lys Asn Leu
        435                 440                 445

AAA TTC ACT ATT TGG GAT GTA GGT GGA AAA CAC AAA TTA AGA CCA TTG    1392
Lys Phe Thr Ile Trp Asp Val Gly Gly Lys His Lys Leu Arg Pro Leu
    450                 455                 460

TGG AAA CAT TAT TAC CTC AAT ACT CAA GCT GTT GTG TTT GTT GTA GAT    1440
Trp Lys His Tyr Tyr Leu Asn Thr Gln Ala Val Val Phe Val Val Asp
465                 470                 475                 480

AGC AGT CAT AGA GAC AGA ATT AGT GAA GCA CAC AGC GAA CTT GCA AAG    1488
Ser Ser His Arg Asp Arg Ile Ser Glu Ala His Ser Glu Leu Ala Lys
                485                 490                 495

TTG TTA ACG GAA AAA GAA CTC CGA GAT GCT CTG CTC CTG ATT TTT GCT    1536
Leu Leu Thr Glu Lys Glu Leu Arg Asp Ala Leu Leu Leu Ile Phe Ala
            500                 505                 510

AAC AAA CAG GAT GTT GCT GGA GCA CTG TCA GTA GAA GAA ATC ACT GAA    1584
Asn Lys Gln Asp Val Ala Gly Ala Leu Ser Val Glu Glu Ile Thr Glu
        515                 520                 525

CTA CTC AGT CTC CAT AAA TTA TGC TGT GGC CGT AGC TGG TAT ATT CAG    1632
Leu Leu Ser Leu His Lys Leu Cys Cys Gly Arg Ser Trp Tyr Ile Gln
    530                 535                 540

GGC TGT GAT GCT CGA AGT GGT ATG GGA CTG TAT GAA GGG TTG GAC TGG    1680
Gly Cys Asp Ala Arg Ser Gly Met Gly Leu Tyr Glu Gly Leu Asp Trp
545                 550                 555                 560

CTC TCA CGG CAA CTT GTA GCT GCT GGA GTA TTG GAT GTT GCT TGATTTAAA  1732
Leu Ser Arg Gln Leu Val Ala Ala Gly Val Leu Asp Val Ala
                565                 570             575
```

```
GGCAGCAGTT GTTTGAAGTT TTGTGGTTAA AAGTAACTTT GCACATAAAA AAAAAAAAAA    1792
AAAATGCATC TCAAAGATG  GTAATTTAGG ATGCATATAT ATATATATAT ATATAAAGGA    1852
ATCTTGGATT GGGAATTCAG TACTTTGCTT TAAAAAATT  TTGTGGCAGA ATTAAATTTC    1912
TAATTGACGC AGATTAGATT GAATTAAATA GAAACTTATT GAATATACAT TCTTTTAAAA    1972
AGTATATTTG TTATTTAAGT TTTTCAGATA ATATGTGACC AATATACTGG GAAAGAGGTA    2032
GTCACAGAGA AAGGGTAAGT GAAGGTTTAT TCTTTCAGTG AAAAAGAAT  AGCCAATTGA    2092
GTGCCTAATG AGACCTCTGT GTGAAGCAAG TGAAGTATAG CTGCTTCTTT TAACCTGCCT    2152
TTTCACTGAA TGTTGGCAGC ATTTAGTAGT AGAAATGACA GTTGCTTAAT GAAATAGAAT    2212
CCAAACTACA TATTTGGATA ATAGGATTAC TTTATGTTTA TGTTCAGAGT TAACAGAACA    2272
CCTTTAATGC TAAGAACTAT AAGGTACAGA AAATTAATAC TTTATATAGT GTTTTATTAA    2332
CTTTCTCCTA CAGCATTTTG TATAAAACAC AATGAGGGAG TGAAATGTTA CCCAATTAGG    2392
CTTGTCAGGT TAGTAATAAA CTGAACAGTA ATAAAACTGT GGAAGTAATT GGATCTGAAT    2452
TTATGAAAGA CCCATTTCCA GGACTGAACC TAGGTCAGAG CTCTAAATTG GTCCTTCTAT    2512
TTTTCAACAA ATTTAAAGTA ATATTTCTTT CTAATATAAT ATTGCATCCT TTGTGGGAAT    2572
```

| | | | | |
|---|---|---|---|---|
| GACTATAGGT | AAAATGTAGT | AAGTAACGCA | GAACCAGGGT | TGGCTTTATT TAAAAGCTAG | 2632 |
| TGACCTAAAT | AGAAAGCGAA | CTTCAAGAGA | AGTTGTAAGT | ACAGTGGCAA ATGCTTATTA | 2692 |
| CTTACTTCAA | ACTGTTTCCC | AAAATAAGTG | CATTTATTTT | GACAATAAAA CTTAAGGCTG | 2752 |
| TTCATGAGAA | GGCCTTGAAA | AGTTACTCTA | GAGGAAAAAT | GTCTAAAGAA AAAAAAAATT | 2812 |
| CAAAAAGTTT | ACATTAATTA | TTCAGTGTTG | TGAGTAAATA | AAAATGTGTG CTCTTTACTG | 2872 |
| TTTTTCATTT | TTAAAGAATA | TTATTATGGA | AGCACGATTT | ATTTAAATAG GTACATTGAG | 2932 |
| ACTTTTTTTT | TTAATGTTCT | GATACATTAG | GATGAAGTTA | AATCTTAAAT CTTATTAGTT | 2992 |
| GAATTGTTGT | AAGGACAGTG | ATGTCTGGTA | ACAAGATGTG | ACTTTTGGT AGCACTGTTG | 3052 |
| TGGTTCATTC | TTTTCAAATC | TATTTTTGTT | TAAAAACAAT | ACAAGTTTTA GAAAACAAAG | 3112 |
| CATTAAAAAA | AAAGCCTATC | AGTATTATGG | GCAATATGTA | AATAAATAAA TGTAATATTT | 3172 |
| CATCCTTTAT | TTTTCAGGTA | AAAGGTCATG | CTGTTACAGG | TGTAGTTTGT GTGCATAAAT | 3232 |
| AATACTTCCG | AATTAAATTA | TTTAATATTT | GACTGATTTC | AATAACTGTG AAAATAAAAA | 3292 |
| GGTGTTGTAT | TGCTTGTGAG | | | | 3312 |

(2) INFORMATION FOR SEQ ID NO:2:

(i) SEQUENCE CHARACTERISTICS:
        (A) LENGTH: 574 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Thr Leu Val Val Asn Lys Leu Gly Ala Gly Val Asp Ser Gly
 1               5                  10                  15

Arg Gln Gly Ser Arg Gly Thr Ala Val Val Lys Val Leu Glu Cys Gly
            20                  25                  30

Val Cys Glu Asp Val Phe Ser Leu Gln Gly Asp Lys Val Pro Arg Leu
        35                  40                  45

Leu Leu Cys Gly His Thr Val Cys His Asp Cys Leu Thr Arg Leu Pro
    50                  55                  60

Leu His Gly Arg Ala Ile Arg Cys Pro Phe Asp Arg Gln Val Thr Asp
65                  70                  75                  80

Leu Gly Asp Ser Gly Val Trp Gly Leu Lys Lys Asn Phe Ala Leu Leu
                85                  90                  95

Glu Leu Leu Glu Arg Leu Gln Asn Gly Pro Ile Gly Gln Tyr Gly Ala
            100                 105                 110

Ala Glu Glu Ser Ile Gly Ile Ser Gly Glu Ser Ile Ile Arg Cys Asp
        115                 120                 125

Glu Asp Glu Ala His Leu Ala Ser Val Tyr Cys Thr Val Cys Ala Thr
    130                 135                 140

His Leu Cys Ser Glu Cys Ser Gln Val Thr His Ser Thr Lys Thr Leu
145                 150                 155                 160

Ala Lys His Arg Arg Val Pro Leu Ala Asp Lys Pro His Glu Lys Thr
                165                 170                 175

Met Cys Ser Gln His Gln Val His Ala Ile Glu Phe Val Cys Leu Glu
            180                 185                 190

Glu Gly Cys Gln Thr Ser Pro Leu Met Cys Cys Val Cys Lys Glu Tyr
        195                 200                 205

Gly Lys His Gln Gly His Lys His Ser Val Leu Glu Pro Glu Ala Asn
    210                 215                 220

Gln Ile Arg Ala Ser Ile Leu Asp Met Ala His Cys Ile Arg Thr Phe
225                 230                 235                 240
```

```
Thr Glu Glu Ile Ser Asp Tyr Ser Arg Lys Leu Val Gly Ile Val Gln
            245                 250                 255
His Ile Glu Gly Gly Glu Gln Ile Val Glu Asp Gly Ile Gly Met Ala
            260                 265                 270
His Thr Glu His Val Pro Gly Thr Ala Glu Asn Ala Arg Ser Cys Ile
            275                 280                 285
Arg Ala Tyr Phe Tyr Asp Leu His Glu Thr Leu Cys Arg Gln Glu Glu
            290                 295                 300
Met Ala Leu Ser Val Val Asp Ala His Val Arg Glu Lys Leu Ile Trp
305                 310                 315                 320
Leu Arg Gln Gln Gln Glu Asp Met Thr Ile Leu Leu Ser Glu Val Ser
            325                 330                 335
Ala Ala Cys Leu His Cys Glu Lys Thr Leu Gln Gln Asp Asp Cys Arg
            340                 345                 350
Val Val Leu Ala Lys Gln Glu Ile Thr Arg Leu Leu Glu Thr Leu Gln
            355                 360                 365
Lys Gln Gln Gln Gln Phe Thr Glu Val Ala Asp His Ile Gln Leu Asp
            370                 375                 380
Ala Ser Ile Pro Val Thr Phe Thr Lys Asp Asn Arg Val His Ile Gly
385                 390                 395                 400
Pro Lys Met Glu Ile Arg Val Val Thr Leu Gly Leu Asp Gly Ala Gly
            405                 410                 415
Lys Thr Thr Ile Leu Phe Lys Leu Lys Gln Asp Glu Phe Met Gln Pro
            420                 425                 430
Ile Pro Thr Ile Gly Phe Asn Val Glu Thr Val Glu Tyr Lys Asn Leu
            435                 440                 445
Lys Phe Thr Ile Trp Asp Val Gly Gly Lys His Lys Leu Arg Pro Leu
    450                 455                 460
Trp Lys His Tyr Tyr Leu Asn Thr Gln Ala Val Val Phe Val Val Asp
465                 470                 475                 480
Ser Ser His Arg Asp Arg Ile Ser Glu Ala His Ser Glu Leu Ala Lys
            485                 490                 495
Leu Leu Thr Glu Lys Glu Leu Arg Asp Ala Leu Leu Leu Ile Phe Ala
            500                 505                 510
Asn Lys Gln Asp Val Ala Gly Ala Leu Ser Val Glu Glu Ile Thr Glu
            515                 520                 525
Leu Leu Ser Leu His Lys Leu Cys Cys Gly Arg Ser Trp Tyr Ile Gln
            530                 535                 540
Gly Cys Asp Ala Arg Ser Gly Met Gly Leu Tyr Glu Gly Leu Asp Trp
545                 550                 555                 560
Leu Ser Arg Gln Leu Val Ala Ala Gly Val Leu Asp Val Ala
            565                 570
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

AATGGGCTGC ATGAATTCAT CCTGTTTTAA        30

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

CCTCCTTCAA TGTGCTGCAC AATTCC        26

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

TGAGTAACTT GAGAACACTC        20

( 2 ) INFORMATION FOR SEQ ID NO:6:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

TGCCCTGCCG GCCACTGTCT ACTCCCGCTC CGAGCTTGTT TA        42

( 2 ) INFORMATION FOR SEQ ID NO:7:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

GACTAGTTCT AGATCGCGAG CGGCCGCCCT TCACCTAGGT CTGTTACTTG TCG        53

( 2 ) INFORMATION FOR SEQ ID NO:8:

( i ) SEQUENCE CHARACTERISTICS:
        ( A ) LENGTH: 33 base pairs ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

GGCCTGGTTC CGCGGATGGC TACCCTGGTT GTA            33

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

GGCCTGGTTC CGCGGATGGA AATTCGGGTC                30

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

CTGCGCCTCG CTCCTCAAGC AACATCCAA                 29

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

CTGCGCCTCG CTCCTTTTGG TCCAATGTG                 29

( 2 ) INFORMATION FOR SEQ ID NO:12:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

ATGGGCCTCA CCAT 14

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

TCTCACTGAT GGCCATAGCA 20

( 2 ) INFORMATION FOR SEQ ID NO:14:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

TCATTTGACA GCCA 14

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

TTGATAGAAT TGGTCTAGGC TTGTTACAAC 30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

GTTGTAACAA GCCTAGACCA ATTCTATCAA 30

( 2 ) INFORMATION FOR SEQ ID NO:17:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

GGCTAAACAG CAACATTGTT CTTGGTAAAC AATAATTGGC AACAAAAC                     48

( 2 ) INFORMATION FOR SEQ ID NO:18:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

TCAGTGAGTT CCAAGGGGGT AACTTTAAAA CATTATTGGT GTGGGCTC                     48

( 2 ) INFORMATION FOR SEQ ID NO:19:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:19:

TGGAATCGGA ACTTCCAGAT CCTCATCGTC CGAGTCCGAT TCACTCTG                     48

( 2 ) INFORMATION FOR SEQ ID NO:20:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:20:

CTCGTGGACG ATGTTGCTGT CGACCCACGC GTCCGT                                  36

( 2 ) INFORMATION FOR SEQ ID NO:21:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

CTCGTGGACG ATGTTGCTGT CGACCCACGC GTCCG　　　　　　　　　　　　35

( 2 ) INFORMATION FOR SEQ ID NO:22:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:22:

TTTGTACAAG ATCGTCGTTT TGCCAGCTGC ATCTAAGCC　　　　　　　　　　39

( 2 ) INFORMATION FOR SEQ ID NO:23:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:23:

GACTAGTTCT AGATCGCGAG CGGCCGCCAC CACCGCTATG GGC　　　　　　　　43

( 2 ) INFORMATION FOR SEQ ID NO:24:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:24:

CTCGTGGACG ATGTGCTGGT CGACAGCTGC CCAAACCGTC TCAG　　　　　　　44

( 2 ) INFORMATION FOR SEQ ID NO:25:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:25:

CTCGTGGACG ATGTGCTGGT CGACGTTAAC ACTCAAAACA GATTT    45

( 2 ) INFORMATION FOR SEQ ID NO:26:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:26:

CTCGTGGACG ATGTGCTGGT CGACTCGAAA AATCATTTTA TTAGGAATAA TTCCA    55

( 2 ) INFORMATION FOR SEQ ID NO:27:

( i ) SEQUENCE CHARACTERISTICS:
        ( A ) LENGTH: 181 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:27:

```
Met Gly Asn Ile Phe Ala Asn Leu Phe Lys Gly Leu Phe Gly Lys Lys
 1               5                  10                  15

Glu Met Arg Ile Leu Met Val Gly Leu Asp Ala Ala Gly Lys Thr Thr
                 20                  25                  30

Ile Leu Tyr Lys Leu Lys Leu Gly Glu Ile Val Thr Thr Ile Pro Thr
             35                  40                  45

Ile Gly Phe Asn Val Glu Thr Val Glu Tyr Lys Asn Ile Ser Phe Thr
     50                  55                  60

Val Trp Asp Val Gly Gly Gln Asp Lys Ile Arg Pro Leu Trp Arg His
 65                  70                  75                  80

Tyr Phe Gln Asn Thr Gln Gly Leu Ile Phe Val Val Asp Ser Asn Asp
                 85                  90                  95

Arg Glu Arg Val Asn Glu Ala Arg Glu Glu Leu Met Arg Met Leu Ala
                100                 105                 110

Glu Asp Glu Leu Arg Asp Ala Val Leu Leu Val Phe Ala Asn Lys Gln
            115                 120                 125

Asp Leu Pro Asn Ala Met Asn Ala Ala Glu Ile Thr Asp Lys Leu Gly
    130                 135                 140

Leu His Ser Leu Arg His Arg Asn Trp Tyr Ile Gln Ala Thr Cys Ala
145                 150                 155                 160

Thr Ser Gly Asp Gly Leu Tyr Glu Gly Leu Asp Trp Leu Ser Asn Gln
                165                 170                 175

Leu Arg Asn Gln Lys
            180
```

( 2 ) INFORMATION FOR SEQ ID NO:28:

( i ) SEQUENCE CHARACTERISTICS:
   ( A ) LENGTH: 181 amino acids
   ( B ) TYPE: amino acid
   ( C ) STRANDEDNESS: single
   ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:28:

```
Met Gly Asn Val Phe Glu Lys Leu Phe Lys Ser Leu Phe Gly Lys Lys
 1               5                  10                  15

Glu Met Arg Ile Leu Met Val Gly Leu Asp Ala Ala Gly Lys Thr Thr
            20                  25                  30

Ile Leu Tyr Lys Leu Lys Leu Gly Glu Ile Val Thr Thr Ile Pro Thr
        35                  40                  45

Ile Gly Phe Asn Val Glu Thr Val Glu Tyr Lys Asn Ile Ser Phe Thr
    50                  55                  60

Val Trp Asp Val Gly Gly Gln Asp Lys Ile Arg Pro Leu Trp Arg His
65                  70                  75                  80

Tyr Phe Gln Asn Thr Gln Gly Leu Ile Phe Val Val Asp Ser Asn Asp
                85                  90                  95

Arg Glu Arg Val Asn Glu Ala Arg Glu Glu Leu Thr Arg Met Leu Ala
            100                 105                 110

Glu Asp Glu Leu Arg Asp Ala Val Leu Leu Val Phe Val Asn Lys Gln
            115                 120                 125

Asp Leu Pro Asn Ala Met Asn Ala Ala Glu Ile Thr Asp Lys Leu Gly
    130                 135                 140

Leu His Ser Leu Arg Gln Arg Asn Trp Tyr Ile Gln Ala Thr Cys Ala
145                 150                 155                 160

Thr Ser Gly Asp Gly Leu Tyr Glu Gly Leu Asp Trp Leu Ser Asn Gln
                165                 170                 175

Leu Lys Asn Gln Lys
            180
```

( 2 ) INFORMATION FOR SEQ ID NO:29:

( i ) SEQUENCE CHARACTERISTICS:
   ( A ) LENGTH: 181 amino acids
   ( B ) TYPE: amino acid
   ( C ) STRANDEDNESS: single
   ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:29:

```
Met Gly Asn Ile Phe Gly Lys Leu Leu Lys Ser Leu Ile Gly Lys Lys
 1               5                  10                  15

Glu Met Arg Ile Leu Met Val Gly Leu Asp Ala Ala Gly Lys Thr Thr
            20                  25                  30

Ile Leu Tyr Lys Leu Lys Leu Gly Glu Ile Val Thr Thr Ile Pro Thr
        35                  40                  45

Ile Gly Phe Asn Val Glu Thr Val Glu Tyr Lys Asn Ile Ser Phe Thr
    50                  55                  60
```

```
Val  Trp  Asp  Val  Gly  Gly  Gln  Asp  Lys  Ile  Arg  Pro  Leu  Trp  Arg  His
 65            70                      75                          80

Tyr  Phe  Gln  Asn  Thr  Gln  Gly  Leu  Ile  Phe  Val  Val  Asp  Ser  Asn  Asp
               85                      90                          95

Arg  Glu  Arg  Val  Asn  Glu  Ala  Arg  Glu  Glu  Leu  Met  Arg  Met  Leu  Ala
              100                     105                         110

Glu  Asp  Glu  Leu  Arg  Asp  Ala  Val  Leu  Leu  Val  Phe  Ala  Asn  Lys  Gln
              115                     120                         125

Asp  Leu  Pro  Asn  Ala  Met  Asn  Ala  Ala  Glu  Ile  Thr  Asp  Lys  Leu  Gly
          130                     135                     140

Leu  His  Ser  Leu  Arg  His  Arg  Asn  Trp  Tyr  Ile  Gln  Ala  Thr  Cys  Ala
 145                    150                     155                         160

Thr  Ser  Gly  Asp  Gly  Leu  Tyr  Glu  Gly  Leu  Asp  Trp  Leu  Ala  Asn  Gln
              165                     170                         175

Leu  Lys  Asn  Lys  Lys
              180
```

( 2 ) INFORMATION FOR SEQ ID NO:30:

( i ) SEQUENCE CHARACTERISTICS:
        ( A ) LENGTH: 180 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:30:

```
Met  Gly  Leu  Thr  Ile  Ser  Ser  Leu  Phe  Ser  Arg  Leu  Phe  Gly  Lys  Lys
 1              5                      10                          15

Gln  Met  Arg  Ile  Leu  Met  Val  Gly  Leu  Asp  Ala  Ala  Gly  Lys  Thr  Thr
               20                      25                          30

Ile  Leu  Tyr  Lys  Leu  Lys  Leu  Gly  Glu  Ile  Val  Thr  Thr  Ile  Pro  Thr
               35                      40                          45

Ile  Gly  Phe  Asn  Val  Glu  Thr  Val  Glu  Tyr  Lys  Asn  Ile  Cys  Phe  Thr
 50                     55                          60

Val  Trp  Asp  Val  Gly  Gly  Gln  Asp  Arg  Ile  Arg  Pro  Leu  Trp  Lys  His
 65            70                      75                          80

Tyr  Phe  Gln  Asn  Thr  Gln  Gly  Leu  Ile  Phe  Val  Val  Asp  Ser  Asn  Asp
               85                      90                          95

Arg  Glu  Arg  Ile  Gln  Glu  Val  Ala  Asp  Glu  Leu  Gln  Lys  Met  Leu  Leu
              100                     105                         110

Val  Asp  Glu  Leu  Arg  Asp  Ala  Val  Leu  Leu  Leu  Phe  Ala  Asn  Lys  Gln
              115                     120                         125

Asp  Leu  Pro  Asn  Ala  Met  Ala  Ile  Ser  Glu  Met  Thr  Asp  Lys  Leu  Gly
          130                     135                     140

Leu  Gln  Ser  Leu  Arg  Asn  Arg  Thr  Trp  Tyr  Val  Gln  Ala  Thr  Cys  Ala
 145                    150                     155                         160

Thr  Gln  Gly  Thr  Gly  Leu  Tyr  Glu  Gly  Leu  Asp  Trp  Leu  Ser  Asn  Glu
              165                     170                         175

Leu  Ser  Lys  Arg
              180
```

( 2 ) INFORMATION FOR SEQ ID NO:31:

( i ) SEQUENCE CHARACTERISTICS:
    ( A ) LENGTH: 180 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:31:

```
Met Gly Leu Thr Val Ser Ala Leu Phe Ser Arg Ile Phe Gly Lys Lys
 1               5                  10                  15

Gln Met Arg Ile Leu Met Val Gly Leu Asp Ala Ala Gly Lys Thr Thr
                 20                  25                  30

Ile Leu Tyr Lys Leu Lys Leu Gly Glu Ile Val Thr Thr Ile Pro Thr
             35                  40                  45

Ile Gly Phe Asn Val Glu Thr Val Glu Tyr Lys Asn Ile Cys Phe Thr
         50                  55                  60

Val Trp Asp Val Gly Gly Gln Asp Lys Ile Arg Pro Leu Trp Arg His
 65                  70                  75                  80

Tyr Phe Gln Asn Thr Gln Gly Leu Ile Phe Val Val Asp Ser Asn Asp
                 85                  90                  95

Arg Glu Arg Val Gln Glu Ser Ala Asp Glu Leu Gln Lys Met Leu Gln
                100                 105                 110

Glu Asp Glu Leu Arg Asp Ala Val Leu Leu Val Phe Ala Asn Lys Gln
                115                 120                 125

Asp Met Pro Asn Ala Met Pro Val Ser Glu Leu Thr Asp Lys Leu Gly
        130                 135                 140

Leu Gln His Leu Arg Ser Arg Arg Trp Tyr Val Gln Ala Thr Cys Ala
145                 150                 155                 160

Thr Gln Gly Thr Gly Leu Tyr Asp Gly Leu Asp Trp Leu Ser His Glu
                165                 170                 175

Leu Ser Lys Arg
            180
```

( 2 ) INFORMATION FOR SEQ ID NO:32:

( i ) SEQUENCE CHARACTERISTICS:
        ( A ) LENGTH: 179 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:32:

```
Met Gly Lys Val Leu Ser Lys Leu Phe Lys Gly Ile Phe Gly Asn Lys
 1               5                  10                  15

Glu Met Arg Ile Leu Met Leu Gly Leu Asp Ala Ala Gly Lys Thr Thr
                 20                  25                  30

Ile Leu Tyr Lys Leu Lys Leu Gly Gln Ser Val Thr Thr Ile Pro Thr
             35                  40                  45

Val Gly Phe Asn Val Glu Thr Val Thr Tyr Lys Asn Val Lys Phe Asn
```

|       |       |       |       |       | 50    |       |       |       |       | 55    |       |       |       |       | 60    |       |       |       |       |
|-------|-------|-------|-------|-------|-------|-------|-------|-------|-------|-------|-------|-------|-------|-------|-------|-------|-------|-------|-------|

```
Val  Trp  Asp  Val  Gly  Gly  Gln  Asp  Lys  Ile  Arg  Pro  Leu  Trp  Arg  His
 65                      70                       75                       80

Tyr  Tyr  Thr  Gly  Thr  Gln  Gly  Leu  Ile  Phe  Val  Val  Asp  Cys  Ala  Asp
                85                       90                       95

Arg  Asp  Arg  Ile  Asp  Glu  Ala  Arg  Gln  Glu  Leu  His  Arg  Ile  Ile  Asn
               100                      105                      110

Asp  Arg  Glu  Met  Arg  Asp  Ala  Ile  Ile  Leu  Ile  Phe  Ala  Asn  Lys  Gln
              115                      120                      125

Asp  Leu  Pro  Asp  Ala  Met  Lys  Pro  His  Glu  Ile  Gln  Glu  Lys  Leu  Gly
         130                      135                      140

Leu  Thr  Arg  Ile  Arg  Asp  Arg  Asn  Trp  Tyr  Val  Gln  Pro  Ser  Cys  Ala
145                      150                      155                      160

Thr  Ser  Gly  Asp  Gly  Leu  Tyr  Glu  Gly  Leu  Thr  Trp  Leu  Thr  Ser  Asn
                   165                      170                      175

Tyr  Lys  Ser
```

( 2 ) INFORMATION FOR SEQ ID NO:33:

( i ) SEQUENCE CHARACTERISTICS:
        ( A ) LENGTH: 187 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:33:

```
Met  Gly  Asn  Ile  Phe  Ala  Asn  Leu  Phe  Lys  Gly  Leu  Phe  Gly  Lys  Lys
 1                    5                       10                       15

Glu  Ile  Arg  Val  Val  Thr  Leu  Gly  Leu  Asp  Gly  Ala  Gly  Lys  Thr  Thr
                20                       25                       30

Ile  Phe  Tyr  Lys  Leu  Gln  Asp  Gly  Glu  Phe  Met  Gln  Pro  Ile  Pro  Thr
               35                       40                       45

Ile  Gly  Phe  Asn  Val  Glu  Thr  Val  Glu  Tyr  Lys  Asn  Leu  Lys  Phe  Thr
         50                       55                       60

Ile  Trp  Asp  Val  Gly  Gly  Lys  His  Lys  Leu  Arg  Pro  Leu  Trp  Lys  His
 65                      70                       75                       80

Tyr  Tyr  Leu  Asn  Thr  Gln  Ala  Val  Val  Phe  Val  Val  Asp  Ser  Ser  His
                85                       90                       95

Arg  Asp  Arg  Ile  Ser  Glu  Ala  His  Ser  Glu  Leu  Ala  Lys  Leu  Leu  Thr
               100                      105                      110

Glu  Lys  Glu  Leu  Arg  Asp  Ala  Leu  Leu  Leu  Ile  Phe  Ala  Asn  Lys  Gln
              115                      120                      125

Asp  Val  Ala  Gly  Ala  Leu  Ser  Val  Glu  Glu  Ile  Thr  Glu  Leu  Leu  Ser
         130                      135                      140

Leu  His  Lys  Leu  Cys  Cys  Gly  Arg  Ser  Trp  Tyr  Ile  Gln  Gly  Cys  Asp
145                      150                      155                      160

Ala  Arg  Ser  Gly  Met  Gly  Leu  Tyr  Glu  Gly  Leu  Asp  Trp  Leu  Ser  Arg
                   165                      170                      175

Gln  Leu  Val  Ala  Ala  Gly  Val  Leu  Asp  Val  Ala
                   180                      185
```

( 2 ) INFORMATION FOR SEQ ID NO:34:

(i) SEQUENCE CHARACTERISTICS:
    (A) LENGTH: 50 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:34:

GACTAGTTCT AGATCGCGAG CGGCCGCCCT GGATATCTAA CCAAGGACAT  50